(12) United States Patent
Ané et al.

(10) Patent No.: US 10,149,472 B2
(45) Date of Patent: Dec. 11, 2018

(54) CHITIN OLIGOMERS FOR USE IN PROMOTING NON-LEGUMINOUS PLANT GROWTH AND DEVELOPMENT

(71) Applicant: Wisconsin Alumni Research Foundation, Madison, WI (US)

(72) Inventors: Jean-Michel Ané, Madison, WI (US); Audrey Kalil, Williston, ND (US); Junko Maeda, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 15/185,587

(22) Filed: Jun. 17, 2016

(65) Prior Publication Data

US 2016/0366883 A1    Dec. 22, 2016

Related U.S. Application Data

(60) Provisional application No. 62/180,953, filed on Jun. 17, 2015.

(51) Int. Cl.
    *A01N 43/16*      (2006.01)

(52) U.S. Cl.
    CPC ..................... *A01N 43/16* (2013.01)

(58) Field of Classification Search
    CPC .... A01N 43/16; A01N 25/10; C08G 59/5026; C09D 163/00
    USPC ....................................................... 504/292
    See application file for complete search history.

(56) References Cited

U.S. PATENT DOCUMENTS

| | | | |
|---|---|---|---|
| 2011/0301032 A1 | 12/2011 | Denarie et al. | |
| 2013/0079224 A1* | 3/2013 | Smith | C05F 11/00 504/101 |

OTHER PUBLICATIONS

Jongho Sun et al. (The Plant Cell, vol. 27: 823-838, Mar. 2015).*
Kazumitsu Miyoshi et al. (Annals of Botany 79: 391-395, 1997).*
Olah et al. ,Nod factors and a diffusible factor from arbuscular mycorrhizal fungi stimulate lateral root formation in Medicago truncatula via the DMI1/DMI2 signaling pathway, Plant Journal (2005), 44(2), 195-207.*
Genre A., et al. (2013) "Short-chain chitin oligomers from arbuscular mycorrhizal fungi trigger nuclear Ca2+ spiking in Medicago truncatula roots, and their production is enhanced by strigolactone." New Phytol 198(1):190-202.
Sun, J., et al. (2015) Activation of Symbiosis Signaling by Arbuscular Mycorrhizal Fungi in Legumes and Rice. The Plant Cell, vol. 27: 823-838.

* cited by examiner

*Primary Examiner* — Johann R Richter
*Assistant Examiner* — Courtney A Brown
(74) *Attorney, Agent, or Firm* — Boyle Fredrickson S.C.

(57) ABSTRACT

Methods for stimulating the growth of non-leguminous plants are disclosed. In the methods, a non-leguminous plant, a part thereof, or a seedling or seed thereof is contacted with a composition comprising a chitooligosaccharide (CO) having the formula:

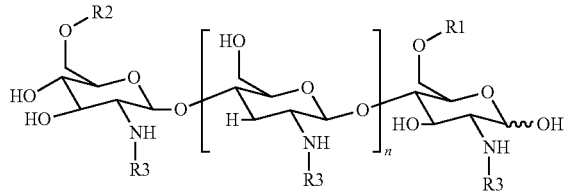

$R_1$ is —H, —$CH_3$, —$COCH_3$, —$SO_3H$, —$SO_3Na$, arabinose, methylated arabinose, fucose, or methylated fucose; $R_2$ is —H, —$CH_3$, —$COCH_3$, —$SO_3H$, —$SO_3Na$, arabinose, methylated arabinose, fucose, or methylated fucose; each $R_3$ is independently —H or —$COCH_3$; and n is 0, 1, 2, 3, 4, 5 or 6. As non-limiting examples, the method can be used to stimulate production and yield in a cereal grain crop plant, such as rice, wheat or corn (maize).

16 Claims, 17 Drawing Sheets

CHITIN OLIGOMERS FOR USE IN PROMOTING NON-LEGUMINOUS PLANT GROWTH AND DEVELOPMENT

CROSS REFERENCE TO RELATED APPLICATIONS

This application claims the benefit of U.S. Provisional Application No. 62/180,953 filed on Jun. 17, 2015, which is incorporated by reference herein in its entirety.

STATEMENT REGARDING FEDERALLY SPONSORED RESEARCH OR DEVELOPMENT

This invention was made with government support under IOS1256664 awarded by the National Science Foundation. The government has certain rights in the invention.

BACKGROUND

This application relates to chitooligosaccharides that lack a lipid moiety, and to methods of using such chitooligosaccharides to promote growth and/or development of non-leguminous plants.

Plants associate with a wide range of microorganisms that facilitate the acquisition of nutrients and protect them against biotic and abiotic stresses. For example, interactions with arbuscular mycorrhizal (AM) fungi are widespread in land plants, and this association aids in the uptake of nutrients from the soil (Harrison, M. J. (2005), Annu. Rev. Microbiol. 59: 19-42). Because AM fungi are obligate symbionts, little is known about the molecular and genetic basis of this symbiosis.

Much of what is known about AM fungi/plant symbiosis has come from studies of the symbiotic association between plants and nitrogen-fixing *rhizobium* bacteria, which most notably results in the formation of nitrogen-fixing nodules. Unlike the association between AM fungi and plants, the *rhizobium* bacteria symbiosis is restricted to specific groups of plants, primarily legumes (Soltis, D. E., et al. (1995), Proc. Natl. Acad. Sci. USA 92: 2647-2651). However, both interactions are similar in that they require chemical communication facilitated by the production of diffusible signals by the symbiont (Oldroyd, G. E. (2013), Nat. Rev. Microbiol. 11: 252-263).

Rhizobial bacteria signal to legumes with Nod factors, which are lipochitooligosaccharides (LCOs) containing a chitin backbone substituted with a lipid moiety, an N-acyl group, and a number of additional groups that vary between Nod factors produced by different species of *rhizobia* (Dénarié, J. et al. (1996), Annu. Rev. Biochem. 65: 503-535). Nod factor perception utilizes a signalling pathway that is also involved in the establishment of mycorrhizal associations (Oldroyd, G. E. (2013)).

AM fungi also produce diffusible signals that are recognized by the host plant via the common symbiosis signalling pathway. Research suggests that at least two different mycorrhizal signals are active on *Medicago truncatula* (Chabaud, M., et al. (2011), New Phytol. 189: 347-355). Similarly, work in rice (*Oryza sativa*) demonstrates mycorrhizal signalling that is both dependent and independent of the common symbiosis signalling pathway (Gutjahr, C., et al. (2008), Plant Cell 20: 2989-3005).

The AM fungus *Rhizophagus irregularis* produces LCOs (Maillet, F., et al. (2011), Nature 469: 58-63), some of which are sulfated, resulting in a structure very similar to the Nod factor produced by *Sinorhizobium meliloti*, the symbiont of *M. truncatula*. These Myc-LCOs activate responses in *M. truncatula* similar to those activated by Nod factor, including the promotion of lateral root outgrowth. Consistent with these findings, U.S. Patent Publication No. 2011/0301032 discloses a method of stimulating a plant by contacting the plant with Myc-LCOs and variants thereof, wherein the variants all retain a lipid moiety.

The lipid moieties incorporated into the LCOs disclosed by, e.g., U.S. Patent Publication No. 2011/0301032, make it difficult and/or expensive to synthesize large quantities of such compounds from commonly available chitooligosaccharide source materials. Furthermore, the lipid moieties decrease the solubility of such compounds in water, increasing the challenges associated with dissolving the compounds in aqueous solutions for scaled up application to seeds, seedlings, or plants. Accordingly, there is a need in the art for alternate compositions and methods for stimulating plant growth and/or development that do not have these disadvantages in large-scale applications.

BRIEF SUMMARY

In addition to LCOs, AM fungi produce short-chain chitooligosaccharides lacking a lipid moiety (COs), such as CO4 and CO5, that may be involved in AM/plant interactions (Genre, A., et al. (2013), New Phytol. 198: 190-202). Furthermore, longer chain COs, such as CO8, are known to function as pathogenic signals that stimulate plant defenses. The inventors disclose herein that both shorter and longer chain COs can be used to promote the growth and/or development of non-leguminous plants, including, without limitation, of cereal grains, such as rice, wheat or corn (maize).

The term "non-leguminous plant" refers to plant species that are not classified as legumes. It is well-known in the art as to which plant species are legumes. The term "cereal grain" refers to a grass that is cultivated as a crop for the edible components of its grain (a type of fruit known in the art as a caryopsis).

Accordingly, in a first aspect, this disclosure encompasses a method for stimulating the growth of a non-leguminous plant. The method includes the step of contacting a non-leguminous plant, a part thereof, or a seedling or seed thereof with a composition that includes a chitooligosaccharide (CO) having the formula:

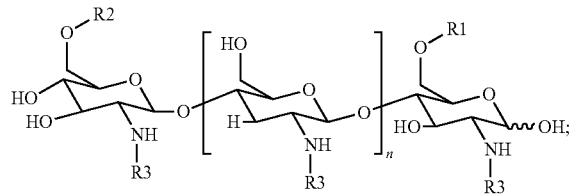

where n is 0, 1, 2, 3, 4, 5, or 6; R1 is —H, —CH$_3$, —COCH$_3$, —SO$_3$H, —SO$_3$Na, arabinose, methylated arabinose, fucose, or methylated fucose; R2 is —H, —CH$_3$, —COCH$_3$, —SO$_3$H, —SO$_3$Na, arabinose, methylated arabinose, fucose, or methylated fucose; and each R3 is independently —H or —COCH$_3$. As a result of practicing the method, the growth of the plant is stimulated.

"Stimulated" plant growth means that the quantity, weight and/or size of one or more parts of the plant is increased, relative to a plant where the seed, seedling, plant, or plant part has not been contacted with the composition that includes the CO. Such increased quantity, size or mass may include, but is not limited to, increased length of the root system, increased number of crown roots, increased number of lateral roots, increased dry weight, increased shoot length, or some combination of these. Such plant growth stimulation can have some beneficial effects on the plant, including, without limitation, enhancing soil nutrient acquisition, facilitating the establishment of young plants in the field, and increasing crop plant yield.

In some embodiments, the composition is contacted with one or more leaf and/or root surfaces of the non-leguminous plant. In some such embodiments, the composition further comprises a surfactant. A "surfactant," also known as a "wetting agent," is a substance that is capable of reducing the surface tension of a liquid composition.

In some embodiments, the composition is contacted with a seedling, seedling part or seed of the non-leguminous plant. In some such embodiments, the seedling, seedling part or seed of the non-leguminous plant is submerged in and subsequently removed from the composition. In some embodiments, the seedling part may include plant foliage or plant roots.

In some embodiments, the composition is contacted with the plant, plant part, seedling or seed for about 1 hour to about 96 hours. In some such embodiments, the composition is contacted with the plant, plant part, seedling or seed for about 6 hours to about 48 hours.

In some embodiments, the concentration of the CO in the composition is within the range of about $10^{-3}$ M to about $10^{-10}$ M. In some such embodiments, the concentration of the CO in the composition is within the range of about $10^{-3}$M to about $10^{-9}$M. In some such embodiments, the concentration of the CO in the composition is within the range of about $10^{-3}$ M to about $10^{-8}$M.

In some embodiments, the composition further includes water and alcohol. The alcohol acts to increase the solubility of the CO in the aqueous composition. In some such embodiments, the alcohol is ethanol.

In some embodiments, the non-leguminous plant is a monocotyledon. In some such embodiments, the monocotyledon is a cereal grain. Non-limiting examples of cereal grains that can be used with the method include rice, wheat and corn (maize).

In some embodiments, R1 is —H, R2 is —H, and each R3 is —COCH$_3$. In some such embodiments, n is 2 (the compound is tetra-N-acetylchitotetraose, CO4) or 6 (the compound is octa-N-acetyl-chitooctaose, CO8).

Other features of the disclosed methods will become apparent from a review of the specification, claims, and drawings.

and two stars (**) indicate significant difference at the P<0.1, P<0.01 level each. (n=10).

Figure 11:
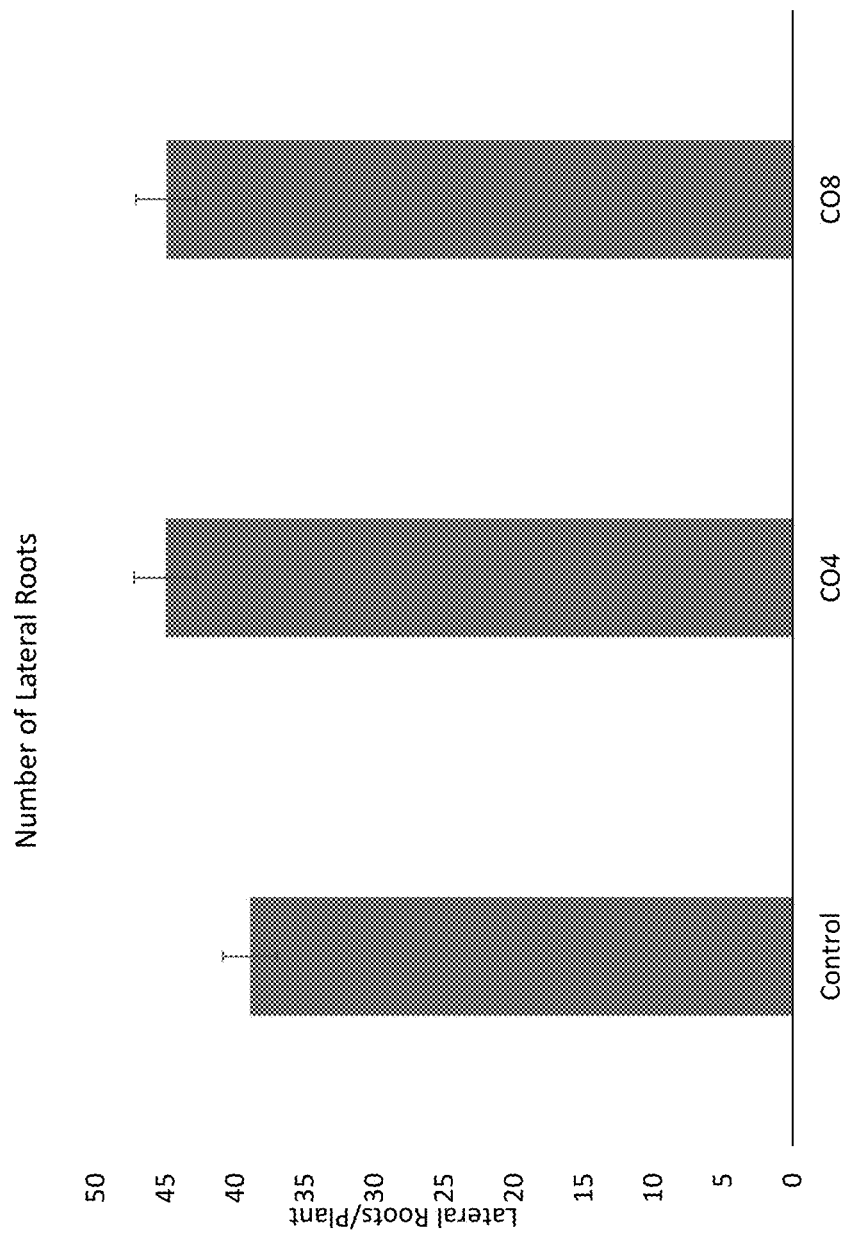

FIG. 11 shows the effect of seed application on corn lateral root development. Compared with control treatment, CO4 treatment significantly promoted lateral root production. One star (*) indicates significant difference at the p<0.1 (n=20).

FIGS. 12 A and 12B show the effect of foliar application on the shoot and root length. Three-weeks-old rice leaves were treated with three different solutions of 0.5% ethanol, $10^{-6}$ M CO4, or $10^{-6}$ M CO8 by painting brushes, and the length of shoots (12A) and roots (12B) were measured at treatment day (12A left bar), 14 days after treatment (12A center bar), and 18 days after treatment (12A right bar and 12B). Both shoot and root lengths of CO4 treated rice were significantly longer than ethanol treated ones at 14 days and 18 days. One star (*) and two stars (**) indicate significant difference at the P<0.1, P<0.01 level each (n=11).

DETAILED DESCRIPTION

A. In General

This invention is not limited to the particular methodology, protocols, or reagents described, as these may vary. The terminology used herein is for the purpose of describing particular embodiments only and is not intended to limit the scope of the present invention, which will be limited only by the appended claims.

As used herein and in the appended claims, the singular forms "a", "an" and "the" include plural reference, unless the context clearly dictates otherwise. As well, the terms "a" (or "an"), "one or more" and "at least one" can be used interchangeably herein. Also, the terms "comprising", "including" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, certain exemplary methods and materials are now described.

B. The Invention

The present invention provides methods and compositions for promoting plant growth and/or development in non-leguminous plants.

The method includes the step of contacting a non-leguminous plant, a part thereof, or a seedling or seed thereof with a composition that includes a chitooligosaccharide (CO), as described above.

The method used for contacting the composition with the plant, part thereof, or seedling or seed thereof (the "target") can include any method known in the art, including, without limitation, spraying the target with the composition, dipping the target into the composition, soaking or submersing the target in the composition, coating the target with the composition, or adding the composition to the soil in proximity to the target, whereby the composition comes in contact with the composition. Optionally, to facilitate the contacting step, the composition is in the form of a liquid, such as an aqueous solution or an oil-based mixture. In such embodiments, the composition may further include a solubilizing agent that increases the solubility of the CO within the liquid composition, and/or a surfactant or wetting agent that facilitates maximum contact between the liquid composition and the plant or seed surface to which it is applied.

The period for which the target is contacted with the composition can vary. In some embodiments, the composition is contacted with the plant, plant part, seedling or seed for about 5 minutes to about a week. Optionally, the contacting step occurs for a period that falls within a range having a lower value of about 10 minutes, about 20 minutes, about 30 minutes, about 40 minutes, about 50 minutes, about one hour, about two hours, about three hours, about four hours, about five hours, about six hours, about seven hours, about eight hours, about nine hours, about ten hours, about eleven hours, or about twelve hours. Optionally, the contacting step occurs for a period that falls within a range having an upper value of about 20 minutes, about 30 minutes, about 40 minutes, about 50 minutes, about one hour, about two hours, about three hours, about four hours, about five hours, about six hours, about seven hours, about eight hours, about nine hours, about ten hours, about eleven hours, about twelve hours, about one day, about two days, about three days, or about four days.

The concentration of the CO in the composition can vary. Optionally, the concentration of the CO within the composition falls within a range having a lower value of about $10^{-4}$ M, about $10^{-5}$ M, about $10^{-6}$ M, about $10^{-7}$ M, about $10^{-8}$ M, about $10^{-9}$ M, about $10^{-10}$ M, about $10^{-11}$ M, or about $10^{-12}$ M. Optionally, the concentration of the CO within the composition falls within a range having an upper value of about $10^{-3}$ M, about $10^{-4}$ M, about $10^{-5}$ M, about $10^{-6}$ M, about $10^{-7}$ M, about $10^{-8}$ M, about $10^{-9}$ M, about $10^{-10}$ M, about $10^{-11}$ M, or about $10^{-12}$ M.

The compositions may include a single type of CO, but may also include mixtures of two or more distinctly different COs, as described above.

C. Examples

The following Examples are offered by way of illustration only, and not by way of limitation.

Example 1: CO4 and CO8 Activate Symbiotic Signalling and Promote Root System Development in Rice Plants establish root symbioses with arbuscular mycorrhizal fungi to facilitate nutrient acquisition. Establishment of this interaction requires plant recognition of diffusible signals from the fungus, including lipochitooligosaccharides (LCOs) and chitooligosaccharides (COs). Nitrogen-fixing *rhizobia* bacteria that form symbioses with leguminous plants also signal to their hosts via LCOs (Nod factors). In legumes, it is thought that both the mycorrhizal and rhizobial symbioses use a common signaling pathway.

In this example, we have assessed the induction of symbiotic signalling processes by the mycorrhizal (Myc)-produced LCOs and COs in rice, a model non-leguminous mycorrhizal plant. We show that the chitin oligomers CO4 and CO8, but not Myc-LCOs, activate symbiotic calcium oscillations in rice atrichoblasts, although CO4 and Myc-LCOs combined were required to induce calcium spiking in root hair cells. In contrast, lateral root emergence was promoted in rice by non-sulphated-LCO (NS-LC), sulphated-LCO (S-LCO), CO4 or CO8, in a DMI3 and POL-LUX dependent manner. Our work demonstrates that COs such as CO4 and CO8 can be used to promote increased root system development in non-leguminous mycorrhizal plants, such as rice.

Introduction

To better understand the mechanisms by which AM fungi signal to non-leguminous host plants, we assessed the induction of symbiotic signalling in rice by the AM produced LCOs and COs. We show in this example that rice appears to respond primarily to COs for activation of calcium oscillations, rather than the LCOs that legumes respond to (although rice does respond to LCOs with the promotion of lateral root emergence). Furthermore, we show for the first time that COs, such as CO4 and CO8, can be used alone or in combination with LCOs to promote root system development in non-leguminous plant species, such as rice. We conclude that COs activate different symbiotic signalling processes in non-leguminous plant species, such as rice, from those activated in legumes.

Materials and Methods

Seed Preparation, Plant Growth Conditions, and Treatment with LCOs and COs.

*Oryza sativa* cv Nipponbare wild-type and Tos17 insertion lines in POLLUX (line NC6453) and DMI3 (line 8513) were used for root architecture experiments (12, 13). Seeds were prepared by sterilizing with 2% bleach for 20 minutes, followed by 3, 5-minute rinses with sterile water. The sterile seeds were then imbibed overnight. Seeds were then plated on damp germination paper in Petri plates under sterile conditions and germinated in the dark at 25 degrees for 7 days. Germinated rice plants were then plated on Fahraeus medium on germination paper and grown at 22 degrees under constant light. After 5 days the plants were treated with $10^{-8}$M LCOs and COs for 24 hours by submersion and re-plated onto Fåhræus Medium 1.5% agar plates (0.132 g/L $CaCl_2$, 0.12 g/L $MgSO_4.7H_2O$, 0.1 g/L $KH_2PO_4$, 0.075 g/L $Na_2HPO_4.2H_2O$, 5 mg/L Fe-citrate, and 0.07 mg/L each of $MnCl_2.4H_2O$, $CuSO_4.5H_2O$, $ZnCl_2$, $H_3BO_3$, and $Na_2MoO_4.2H_2O$, adjusted to pH 6.5 before autoclaving). As all signals were suspended in 50% ethanol, the appropriate concentration of ethanol in sterile DI water served as a control. Root system architecture was assessed after 2 weeks.

Calcium Imaging.

Mycorrhizal induced calcium responses were measured as described previously (14). Transgenic *Oryza sativa* Nipponbare lines carrying Yellow Cameleon 3.6 (YC3.6) FRET-based calcium sensor was used to detect calcium spiking. YC3.6 was imaged on a Nikon Eclipse Ti inverted microscope (Nikon, Japan) equipped with an OptoLED Illuminator (model OptoLED, Cairn Research Ltd, UK). YC3.6 was excited at a wavelength of 455 nm using a royal blue LED and was captured with a charge-coupled device (CCD) camera (model RETIGA-SRV, Qimaging, Canada). Emitted fluorescence was separated by an image splitter with a dichroic mirror (model Optosplit II, Cairn Research Ltd, UK) and then passed through a fluorescence filter set. Images were collected every 5 seconds with 1-second exposure and analyzed using MetaFluor (Molecular Devices, Sunnyvale, Calif., USA).

Mathematical Analysis of Calcium Oscillations.

For Bayesian Spectrum Analysis we computed the most probable periods in the time series following published procedures (15). Ten traces per treatment were analyzed. The joint distributions over the period were used to characterize each group. The plots show binned data to summarize the key periods. These ten traces per treatment were also analyzed for interspike intervals. The point of maximum height for each spike was computed after detrending of the time series using a moving average algorithm. The distances between these maxima gave rise to an interspike distribution. We used the non-parametric Mann-Whitney U-test, also known as the Mann-Whitney-Wilcoxon test (16, 17) to test for significant differences between the distributions.

Three traces per treatment, with approximately 80 spikes altogether, were analyzed for calcium spike characteristics. The time series had an interval of 5 seconds between data points. The traces were detrended using a moving average algorithm (18). We then characterized the spikes by the time required for each upward and downward phase. This was computed by the number of data points it took from the maximum spike height to the baseline fluctuation of the trace. The plots show the mean value of the upward and downward phases for each treatment, and the associated standard deviations are indicated by the error bars.

Measurements of Root Architecture Modifications.

Total lateral roots of rice were enumerated manually two weeks after application of $10^{-8}$M COs and LCOs. As COs and LCOs were suspended in 50% ethanol, the control is sterile deionized water containing the appropriate amount of ethanol. Lateral roots were defined as large and fine lateral roots emerging from crown roots, as well as fine lateral roots emerging from large lateral roots. Root system length was measured starting from the root-shoot junction to the tip of the longest root. The number of crown roots was assessed manually as those roots emerging from the root-shoot junction. Root type characterizations were based upon the descriptions in Gutjahr et al. (19). Data were assessed for normality using the Shapiro-Wilk test ($\alpha$=0.01), and statistical significance was determined using a paired t-test assuming unequal variances, or a Mann-Whitney-Wilcoxon Test if normality was not observed ($\alpha$=0.05). All statistical analysis was conducted using the R software package (20).

Results

Activation of Calcium Oscillations by Myc-LCOs and COs in Rice.

Mycorrhizal fungi associate with a wide range of plant species, and at least in rice this association is dependent on the common symbiosis signalling pathway (12, 21-23). Hence, non-legumes should be able to recognize the mycorrhizal produced LCOs and/or COs. Two major species of LCOs have been characterized from exudates of *R. irregularis*: LCO-IV (C16:0, S or C18:1, S), which we will refer to as sulfated (S)-LCO and LCO-IV (C16:0 or C18:1), which we will refer to as non-sulfated (NS)-LCO (24). For this study, we used S-LCOs and NS-LCOs that were either purified from *R. irregularis* exudates or were synthesized in genetically-modified bacteria as previously described (24). To define the activation of the symbiosis signalling pathway by the AM-produced LCOs and COs, we assessed their ability to activate calcium oscillations, the pathway's earliest measurable event (3).

Figure 1:
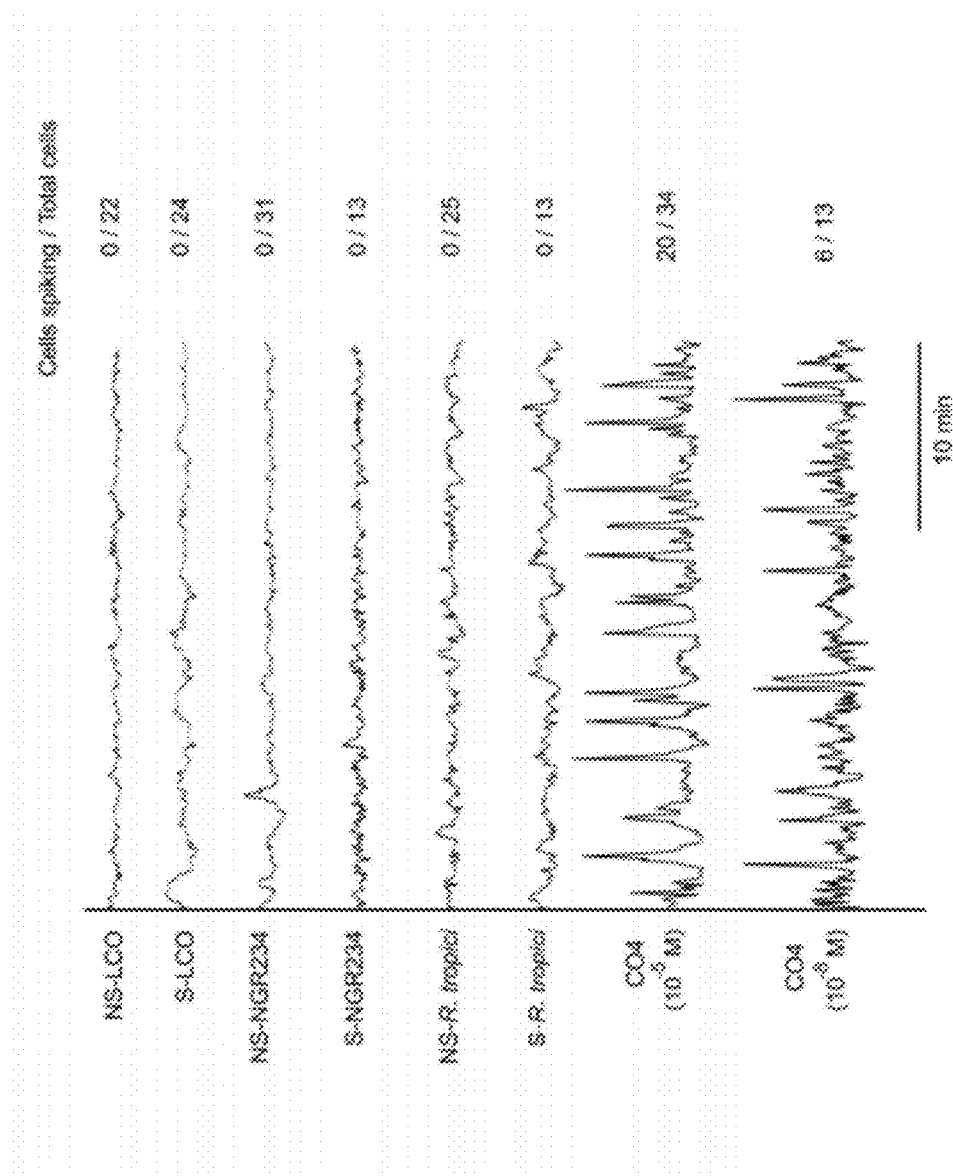
FIG. 1 shows calcium spiking in rice in response to Myc-LCOs, Nod factors, and CO4. Representative calcium traces from rice atrichoblasts on lateral roots treated with $10^{-8}$M Myc-LCOs and LCO isolations from *Rhizobium* sp. NGR234 and *R. tropici*, as well as $10^{-5}$ M and $10^{-8}$M treatments of CO4. The number of cells showing calcium spiking, relative to the total number of cells analyzed is indicated.
Figure 2:
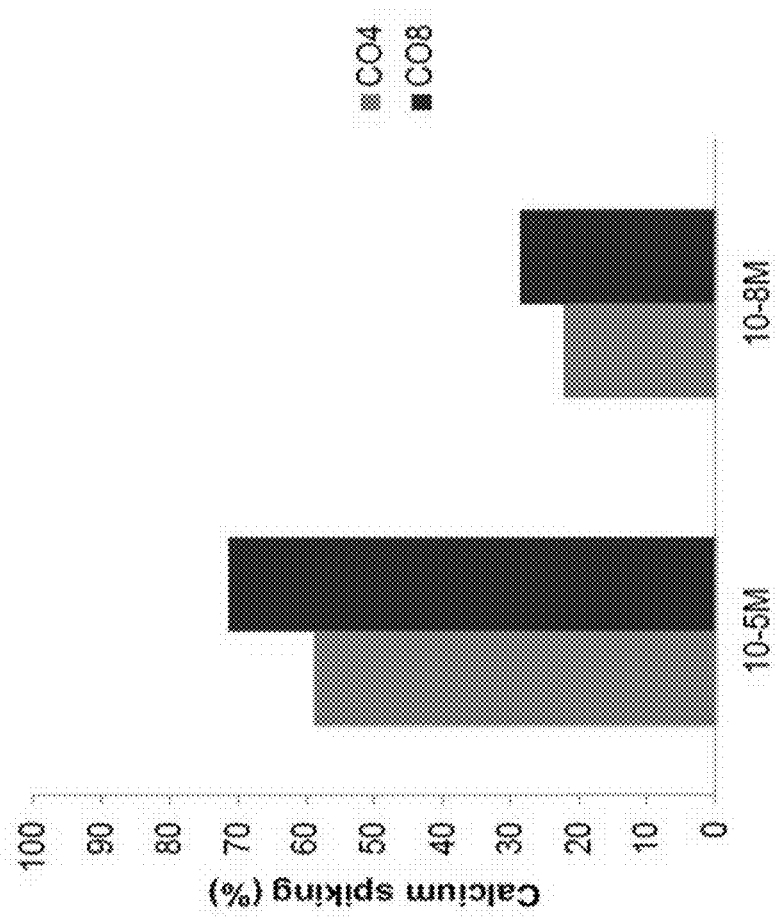
FIG. 2 shows calcium spiking in rice in response to CO4 and CO8. Representative calcium traces from rice atrichoblasts on lateral roots treated with $10^{-8}$M and $10^{-5}$ M CO4 and CO8. Plants appear to respond equally well to CO4 as to CO8.

Calcium responses were assessed using a stably transformed line of *Oryza sativa* cv Nipponbare carrying YC3.6. AM fungi have been shown to predominantly colonize the large lateral roots (19), and therefore, we focused on this root type. No calcium responses were observed following treatment with any of the LCOs assessed, but strong calcium oscillations were observed following treatment with $10^{-5}$M CO4 (FIG. 1). To test an array of different LCO structures, we analyzed calcium spiking in response to Nod factor isolations from the broad host range rhizobial species, *Rhizobium* sp. NGR234, as well as *Rhizobium tropici*, in addition to the Myc-LCOs. Considering that these LCO treatments were performed with $10^{-5}$M, we are confident that rice does not respond to the Nod factors or Myc factors tested. Treatments with $10^{-8}$M CO4 still showed calcium oscillations in rice epidermal cells, but the robustness of the response was reduced and the number of responsive cells was also reduced (FIG. 1). Unlike results reported in *M. truncatula*, rice appears to respond equally well to both CO4 and CO8 with calcium oscillations (FIG. 2).

Mycorrhizal LCOs and COs Induce Rice Root Architecture Modification.

Figure 3A:
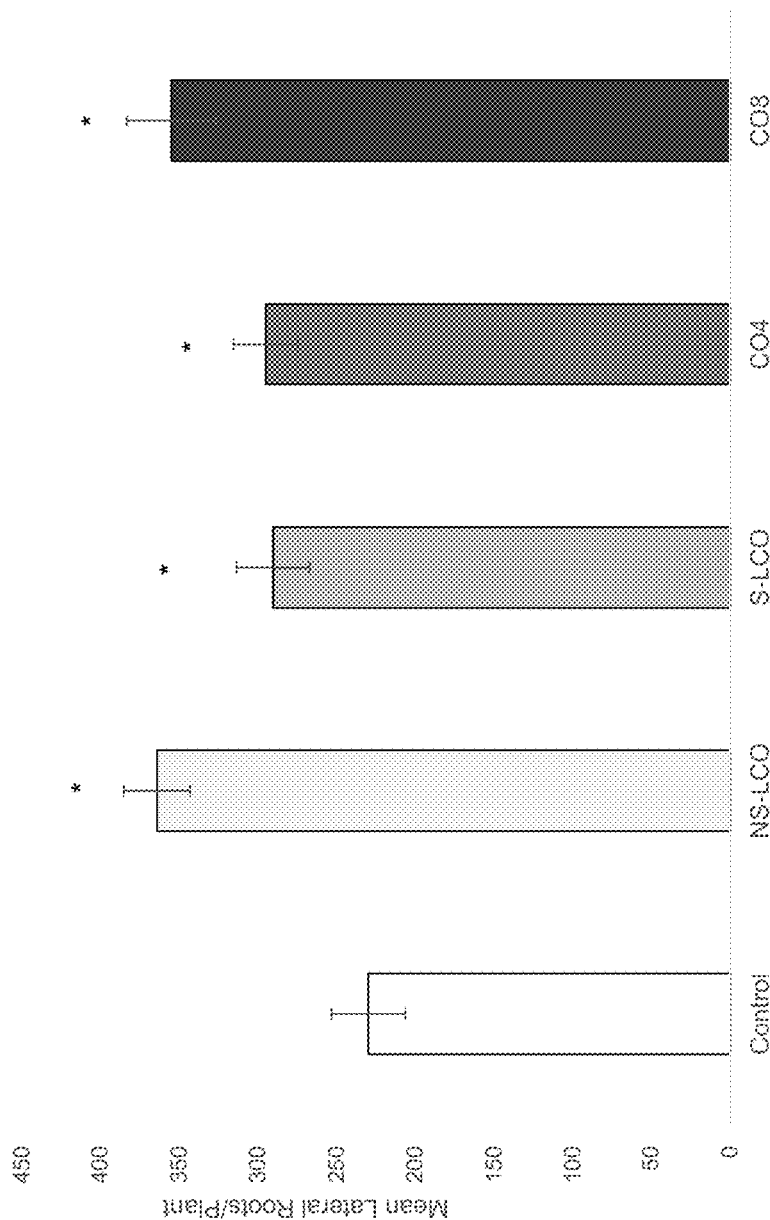
FIGS. 3A, 3B, and 3C show promotion of root system development in rice by NS-LCO, S-LCO, CO4, and CO8. The mean number of lateral roots (FIG. 3A), the length of the root system (FIG. 3B) and the number of crown roots (FIG. 3C) produced per rice plant is shown in response to treatments of $10^{-8}$M COs or LCOs. Plants were treated for 24 hours and then grown for two weeks before assessment. Results displayed are based on at least two replicated experiments (n≥28). The p-value was calculated using a t-test, assuming a normal distribution of the data, or a Wilcoxon signed-rank test when a normal distribution was not observed. Significance was determined within a 95% confidence interval. Error bars indicate standard error.
Figure 3B:
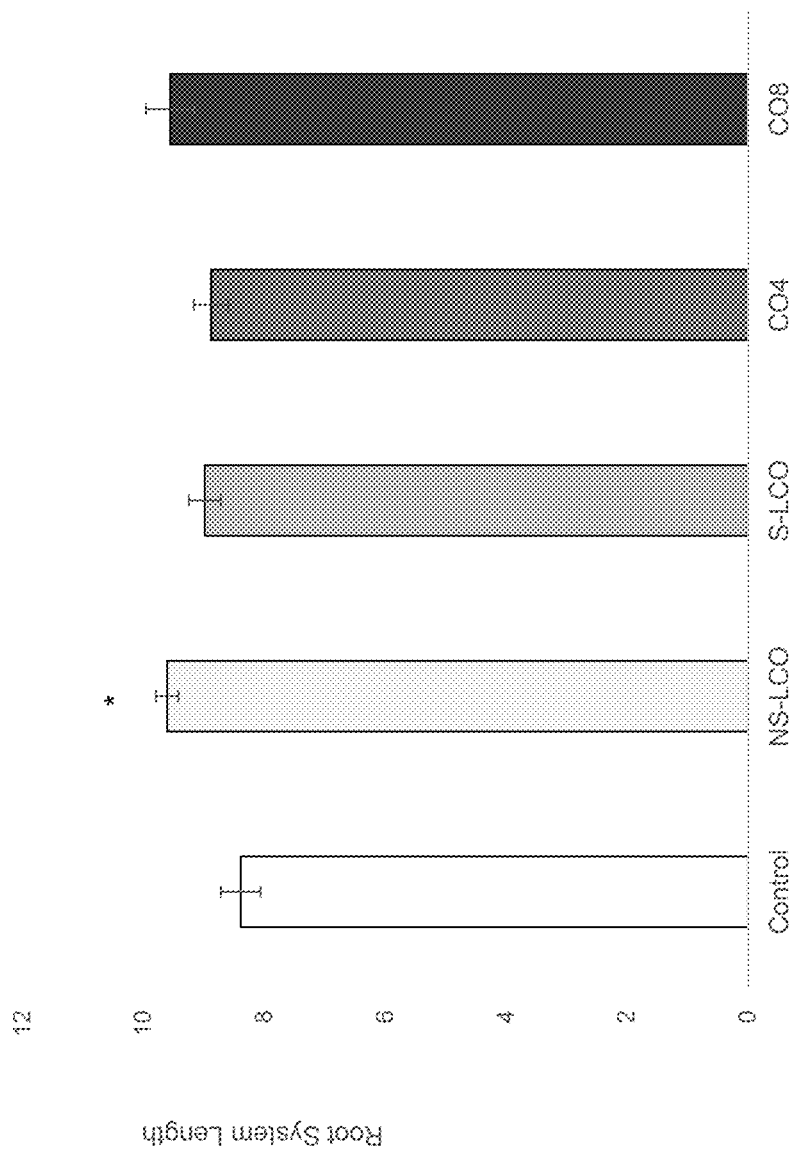
Figure 3C:
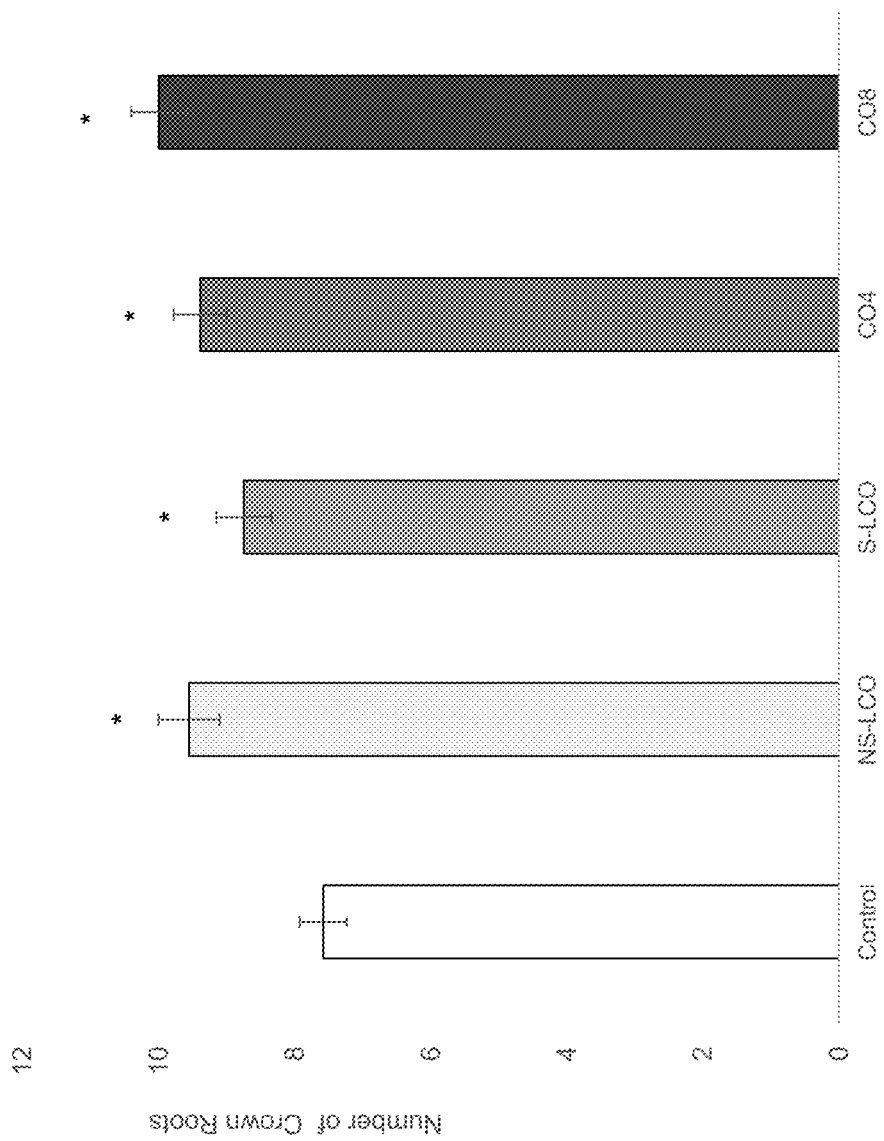

Rice has been shown to respond to AM fungi and exudates from the spores of AM fungi, with changes to root structure, in particular, the promotion of lateral root outgrowth (19, 25). These responses were independent of the common symbiosis signalling pathway. In contrast, we have observed CO4 and CO8 induction of the common symbiosis signalling pathway in rice as measured by the activation of calcium oscillations. In an attempt to understand these seemingly contradictory results, we tested the promotion of lateral root outgrowth in rice by S-LCO, NS-LCO, CO4 and CO8. This study showed that NS-LCO, S-LCO, CO4 and CO8 all promoted lateral and crown root growth in rice (FIG. 3). Interestingly, root system length was only enhanced upon application of NS-LCOs (FIG. 3). These results imply that COs and LCOs activate two modalities of signalling in rice: calcium oscillations that are activated by COs and a separate signalling pathway activated by both LCOs and COs that is associated with changes to root architecture.

Root Architecture Modification by COs and LCOs are DMI3 and POLLUX Dependent.

Figure 4A:
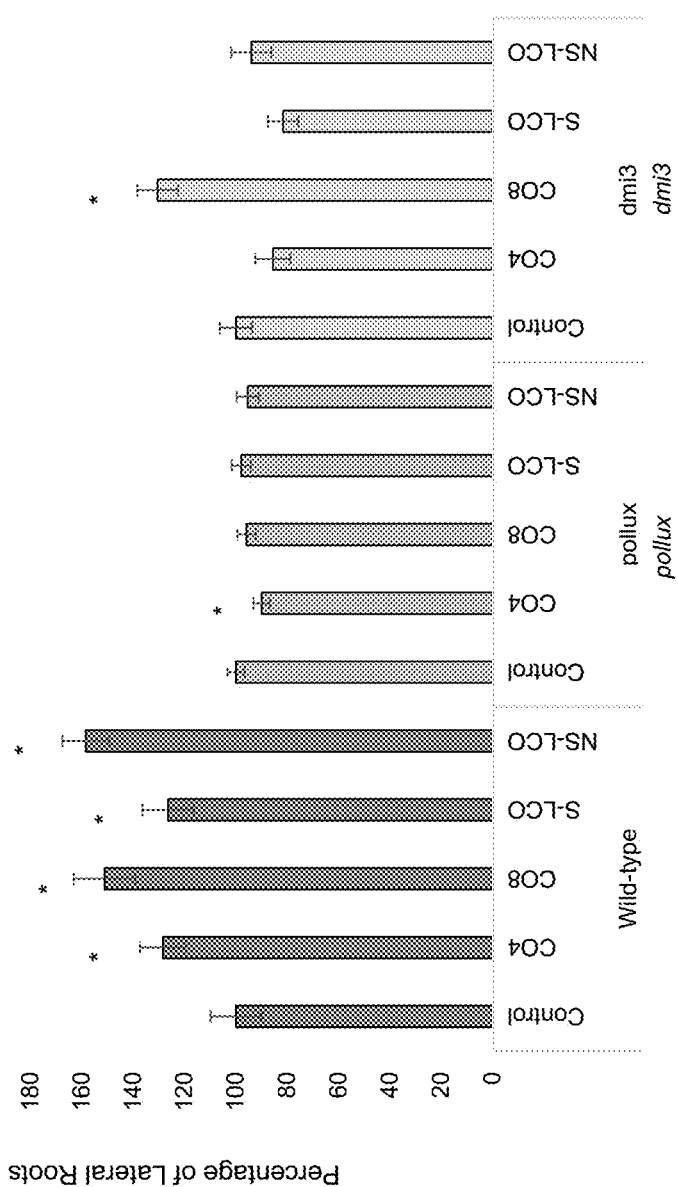
FIGS. 4A, 4B, and 4C show that lateral root induction is dependent upon the symbiotic signalling pathway. The mean percentage of lateral roots (FIG. 4A), the length of the root system (FIG. 4B) and the number of crown roots (FIG. 4C) produced per rice plant is shown in response to treatments of $10^{-8}$M COs or LCOs in wild-type rice plants as well as Ospollux and Osdmi3 mutants. Plants were treated for 24 hours and then grown for two weeks before assessment. Results displayed are based on at least two replicated experiments and calculated as percentage over average of the control treatment (n≥28). The p-value was calculated using a t-test, assuming a normal distribution of the data, or a Wilcoxon signed-rank test when a normal distribution was not observed. Significance was determined within a 95% confidence interval. Error bars indicate standard error.
Figure 4B:
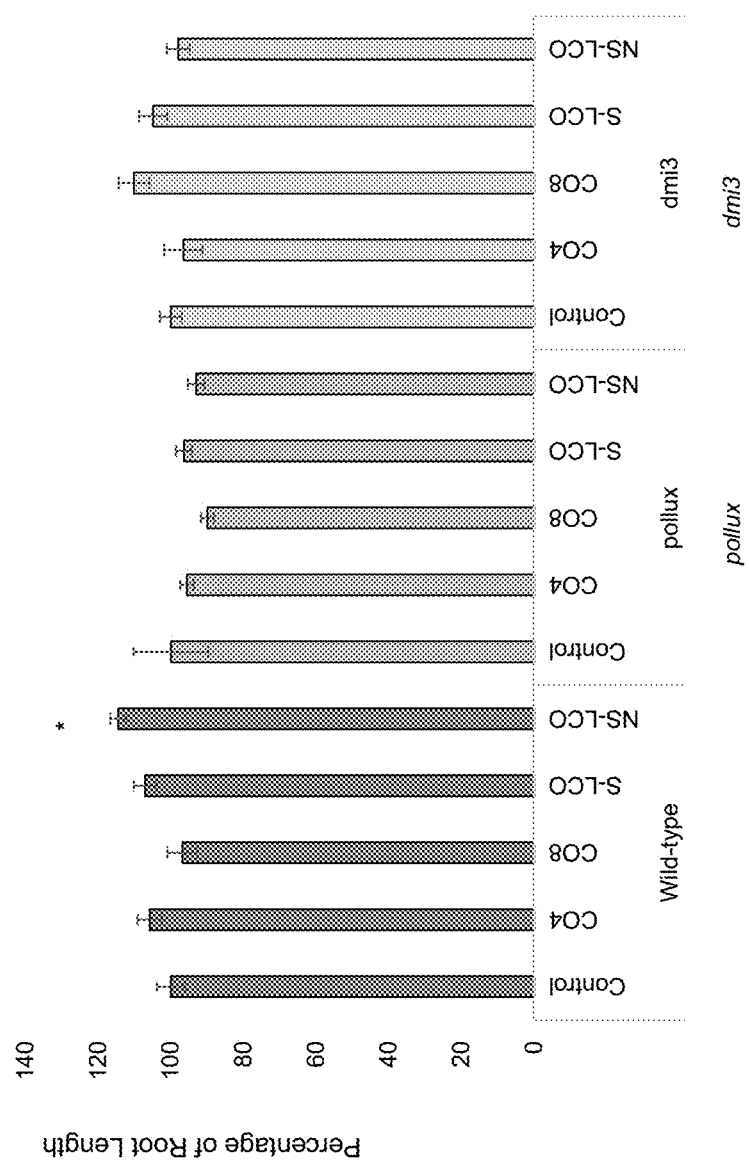
Figure 4C:
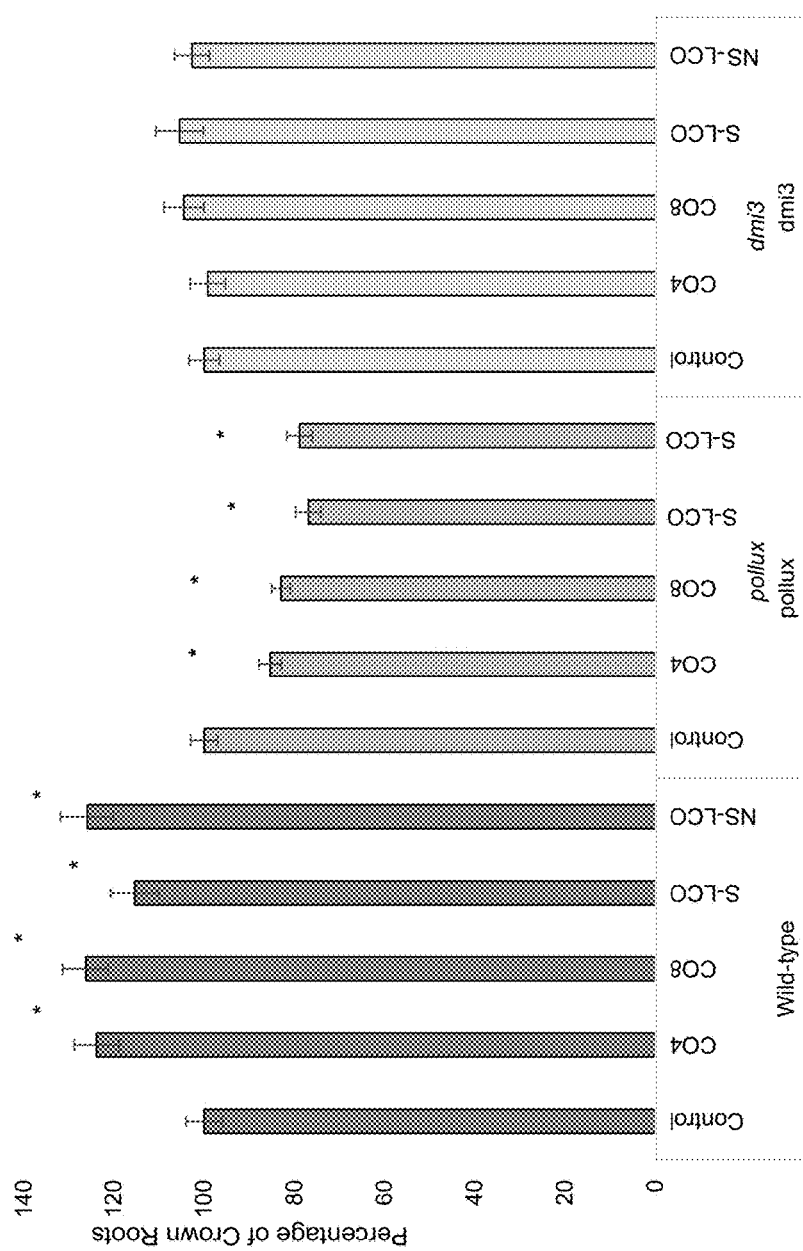

To assess the role of the common symbiotic pathway in regulating root architecture modifications in response to purified LCOs and COs, we quantified root responses to mycorrhizal signals in rice knock-out mutants of pollux (upstream of calcium spiking) and dmi3 (downstream of calcium spiking). We found that lateral root growth promotion by LCOs and CO4 was dependent on both POLLUX and DMI3, while the response to CO8 was dependent on POLLUX (FIG. 4). The increase in crown root growth by both LCOs and COs was dependent upon DMI3 and POLLUX, and there were significantly fewer crown roots in response to all treatments in the pollux mutant (FIG. 4). Finally, the overall root length increase observed in response to NS-LCO was dependent upon both POLLUX and DMI3 (FIG. 4). These results demonstrate that root architecture changes in response to purified mycorrhizal signals require proteins of the common symbiotic pathway.

Figure 5:
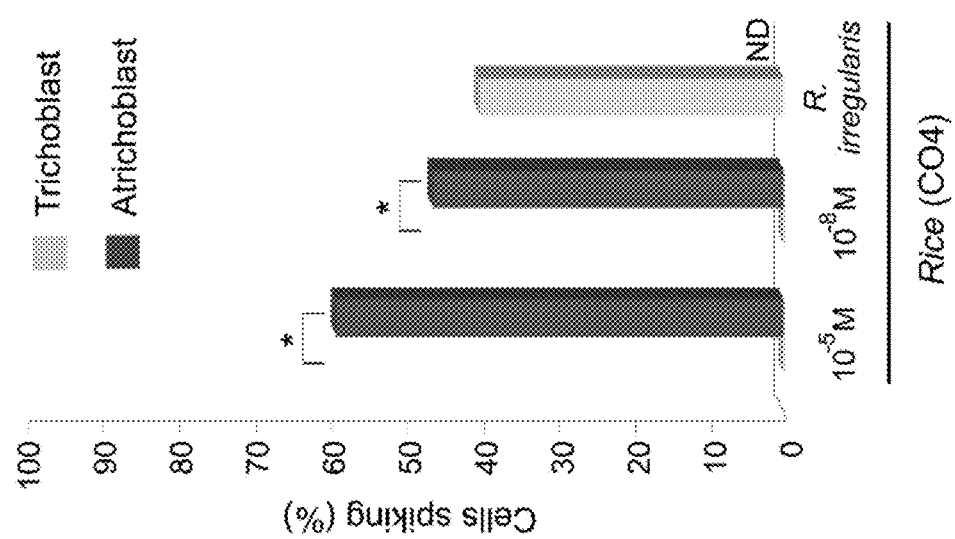
FIG. 5 shows induction of calcium spiking in rice trichoblasts and atrichoblasts. The graph shows the percentage of calcium responsive cells among trichoblasts and atrichoblasts of rice. Treatments of $10^{-5}$ M and $10^{-8}$ M CO4 and the response of trichoblasts near *R. irregularis* hyphae were analyzed.
Figure 6:
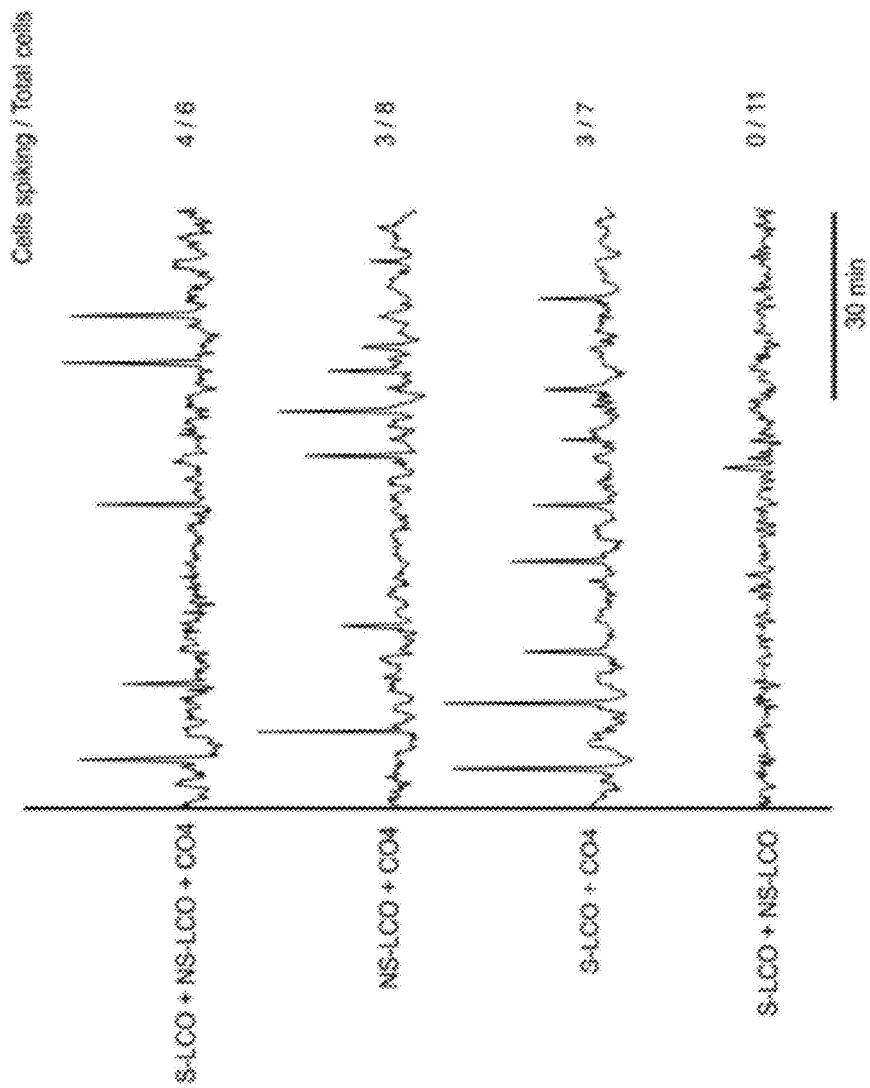
FIG. 6 shows calcium responses to LCOs and COs in rice trichoblasts with representative calcium traces of root hair cells (trichoblasts) treated with mixes of $10^{-8}$ M CO4, S-LCO, and NS-LCO. Note that mixes of Myc-LCOs with CO4 induced calcium oscillations, but the Myc-LCOs alone did not. The number of cells showing calcium responses, relative to the total number of cells analyzed is indicated.

Both LCOs and COs are Required to Induce Calcium Spiking in Trichoblasts. *Rhizobia* colonize legumes by root hair cells (trichoblasts), whereas AM fungi colonize roots via non-root hair epidermal cells (atrichoblasts). Thus, these different root epidermal cell types may respond differently to COs and LCOs. To test this, we directly compared trichoblast and atrichoblast responses using high concentrations of CO4 in rice. Calcium oscillations observed in rice following treatments of CO4 were restricted to atrichoblasts, with no responses in trichoblasts even with CO4 treatments of $10^{-5}$ M (FIG. 5). This preferential nature of rice atrichoblasts to respond to the AM signals is consistent with a preference for AM fungi to colonize the root via atrichoblasts (26). It is possible that either AM fungi produce signalling molecules other than S-LCO, NS-LCO and CO4 that induce calcium oscillations in rice trichoblasts, or that the mix of signalling molecules is important. To test this, we assessed induction of calcium oscillations by an equimolar mix of $10^{-5}$ M S-LCO, NS-LCO, and CO4. Strikingly, we observed calcium spiking in rice root hair cells when treated with this mix of signal molecules, yet these signal molecules, when applied individually at 10-5 M, did not induce calcium spiking (FIG. 6).

Discussion

COs and LCOs Act Synergistically as Symbiotic Signals in Rice.

AM fungi signal to the host plant via diffusible signals (14, 25-27), and at least some of these signals are LCOs (24) and COs (9). In this example, we show that the AM-produced COs can activate calcium oscillations in rice. S-LCO and NS-LCO were purified from exudates of AM fungi based on their capability to activate symbiotic responses in *M. truncatula* that were dependent on the common symbiosis signalling pathway (24). The fact that these LCOs do not trigger calcium spiking in rice may reflect this selectivity in their initial identification. However, rice can sense LCOs since the mix of Myc-LCOs and CO4 activated calcium oscillations in rice root hair cells and LCOs can also promote lateral and crown root growth. Therefore, the absence of calcium responses in rice to the LCO treatments alone does not indicate a lack of response of LCOs by rice.

Our work has revealed a close correlation between the cell-type and its responsiveness to LCOs and CO4. We observed that calcium responses to COs were restricted to atrichoblasts in rice. This preferential response in atrichoblasts correlates well with a preferential colonization of atrichoblasts by AM fungi (26). However, we observed calcium oscillations in rice trichoblasts in treatments where LCOs and CO4 were combined. It would appear that responses in rice trichoblasts are at least partially explained by the mix of LCOs and CO4 produced by the AM fungus. Interestingly, it was shown some years ago that a mix of Nod factors and COs was better at inducing nodulation associated gene expression in soybean than Nod factor treatments alone (28). Perhaps these earlier observations reflect responses to AM fungi, rather than what was previously thought to be a rhizobial response. Alternatively, a mix of LCOs and COs may be relevant in rhizobial interactions as well as AM associations.

Multiple Pathways Mediate LCO and CO Responses in Rice.

We established that rice can distinguish between LCOs, CO4, and CO8, and responds accordingly with either calcium oscillations and/or root architecture modifications. The fact that rice responds to AM fungi with at least two separate signalling pathways has already been shown (23), and the promotion of lateral roots by AM fungi in a manner independent of the common symbiosis signalling pathway was also already shown (25). Thus, there is ample evidence in rice for two pathways of symbiosis signalling. Our work shows that root architecture modification in response to LCOs and CO4 requires the common symbiotic pathway; however, CO8 does not require DMI3. The ability of AM fungi to stimulate lateral root emergence independent of the symbiotic pathway may indicate that the plant responds differently to a mixture of signals and stimuli than it does to purified signals and that during symbiosis the pathway governing root architecture modification does not require calcium spiking to be initiated.

In *Arabidopsis*, lateral root development is under the control of auxin signalling modules. Under high auxin conditions, lateral root founder cells polarize and divide (29). Further rounds of cell division result in lateral root emergence at specific sites in the root. The process leading to lateral root emergence is similar in rice and using the DR5:GUS auxin reporter system, auxin was shown to accumulate in emerging lateral roots (30). Under high auxin concentrations, AUX/IAA proteins are degraded. AUX/IAA proteins repress ARF transcriptional activators, and thus their degradation leads to the transcription of auxin-responsive genes (29). Auxin positively regulates lateral root formation, as a rice plant containing a constitutively active version of IAA13 has fewer lateral roots than wild type (31). Interestingly, auxin signalling is also implicated in the production of crown roots in rice (32, 33). It seems likely, therefore, that the application of LCOs and COs activates the auxin-dependent lateral root and crown root emergence programs. Given that this phenotype was dependent on DMI3 and POLLUX in the case of Myc-LCOs and CO4, it may be that there is cross talk between the common symbiosis pathway and auxin signaling, which results in increased lateral root emergence and crown root growth. Assessing expression of auxin-responsive genes in Ospollux and Osdmi3 mutants in response to COs and LCOs may reveal the mechanisms of this signalling pathway.

CONCLUSION

AM fungi have the distinctive capability of colonizing a broad group of plants. In this example, we demonstrate that CO4 and CO8 form at least part of the spectrum of AM symbiotic signals that can be recognized by a variety of plant species to activate a range of symbiotic signalling processes. More specifically, both CO4 and CO8 can be used to promote increased root system development in non-leguminous plants, such as rice.

REFERENCES CITED

1. Harrison M J (2005) Signaling in the arbuscular mycorrhizal symbiosis. *Annu Rev Microbiol* 59:19-42.
2. Soltis D E, et al. (1995) Chloroplast gene sequence data suggest a single origin of the predisposition for symbiotic nitrogen fixation in angiosperms. *Proc Natl Acad Sci USA* 92(7):2647-2651.
3. Oldroyd G E (2013) Speak, friend, and enter: signaling systems that promote beneficial symbiotic associations in plants. *Nat Rev Microbiol* 11(4):252-263.
4. Denarie J, Debelle F, & Prome J C (1996) *Rhizobium* lipo-chitooligosaccharide nodulation factors: signaling molecules mediating recognition and morphogenesis. *Annu Rev Biochem* 65:503-535.
5. Maillet F, et al. (2011) Fungal lipochitooligosaccharide symbiotic signals in arbuscular mycorrhiza. *Nature* 469 (7328):58-U1501.
6. Ehrhardt D W, Wais R, & Long S R (1996) Calcium spiking in plant root hairs is responding to *Rhizobium* nodulation signals. *Cell* 85(5):673-681.
7. Kosuta S, et al. (2008) Differential and chaotic calcium signatures in the symbiosis signaling pathway of legumes. *Proc Natl Acad Sci USA* 105(28):9823-9828.
8. Sieberer B J, et al. (2009) A nuclear-targeted Cameleon demonstrates intranuclear Ca2+ spiking in *Medicago truncatula* root hairs in response to rhizobial nodulation factors. *Plant Physiol* 151(3):1197-1206.
9. Genre A, et al. (2013) Short-chain chitin oligomers from arbuscular mycorrhizal fungi trigger nuclear Ca2+ spiking in *Medicago truncatula* roots, and their production is enhanced by strigolactone. *New Phytol* 198(1):190-202.
10. Nars A, et al. (2013) *Aphanomyces euteiches* cell wall fractions containing novel glucan-chitosaccharides induce defense genes and nuclear calcium oscillations in the plant host *Medicago truncatula*. *PLoS One* 8(9): e75039.
11. Genre A, et al. (2013) Short-chain chitin oligomers from arbuscular mycorrhizal fungi trigger nuclear Ca2+ spiking in *Medicago truncatula* roots, and their production is enhanced by strigolactone. *New Phytologist* 198(1):179-189.
12. Chen C, Gao M, Liu J, & Zhu H (2007) Fungal symbiosis in rice requires an ortholog of a legume common symbiosis gene encoding a Ca2+/calmodulin-dependent protein kinase. *Plant Physiol* 145(4):1619-1628.
13. Chen C, Fan C, Gao M, & Zhu H (2009) Antiquity and Function of CASTOR and POLLUX, the Twin Ion Channel-Encoding Genes Key to the Evolution of Root Symbioses in Plants. *Plant Physiology (Rockville)* 149(1):306-317.
14. Kosuta S, et al. (2008) Differential and chaotic calcium signatures in the symbiosis signaling pathway of legumes. *Proc Natl Acad Sci USA* 105(28):9823-9828.
15. Granqvist E, Oldroyd G E, & Morris R J (2011) Automated Bayesian model development for frequency detection in biological time series. *BMC Syst Biol* 5:97.
16. Wilcoxon F (1945) Individual comparisons by ranking methods. *Biometrics Bulletin* 1(60):80-83.
17. Mann H & Whitney D (1947) On a Test of Whether one or Two Random Variables is Stochastically Larger than the Other. *Annals of Mathematical Statistics* 18(1):50-60.
18. Brockwell P & R A D (2002) *Introduction to Time Series and Forecasting*.
19. Gutjahr C, Casieri L, & Paszkowski U (2009) *Glomus intraradices* induces changes in root system architecture of rice independently of common symbiosis signaling. *New Phytologist* 182(4):829-837.
20. Team R D C (2008) *R: A language and environment for statistical computing* (R Foundation for Statistical Computing, Vienna, Austria).
21. Banba M, et al. (2008) Divergence of evolutionary ways among common Sym genes: CASTOR and CCaMK show functional conservation between two symbiosis systems and constitute the root of a common signaling pathway. *Plant Cell Physiol* 49(11): 1659-1671.
22. Chen C, Ane J M, & Zhu H (2008) OsIPD3, an ortholog of the *Medicago truncatula* DMI3 interacting protein IPD3, is required for mycorrhizal symbiosis in rice. *New Phytol* 180(2):311-315.
23. Gutjahr C, et al. (2008) Arbuscular mycorrhiza-specific signaling in rice transcends the common symbiosis signaling pathway. *Plant Cell* 20(11):2989-3005.
24. Maillet F, et al. (2011) Fungal lipochitooligosaccharide symbiotic signals in arbuscular mycorrhiza. *Nature* 469 (7328):58-63.
25. Mukherjee A & Ane J M (2011) Germinating spore exudates from arbuscular mycorrhizal fungi: molecular and developmental responses in plants and their regulation by ethylene. *Mol Plant Microbe Interact* 24(2):260-270.
26. Chabaud M, et al. (2011) Arbuscular mycorrhizal hyphopodia and germinated spore exudates trigger Ca2+ spiking in the legume and nonlegume root epidermis. *New Phytologist* 189(1):347-355.
27. Kosuta S, et al. (2003) A diffusible factor from arbuscular mycorrhizal fungi induces symbiosis-specific MtENOD11 expression in roots of *Medicago truncatula*. *Plant Physiology* 131(3):952-962.
28. Minami E, et al. (1996b) Cooperative action of lipo-chitin nodulation signals on the induction of the early nodulin, ENOD2, in soybean roots. *Molecular Plant-Microbe Interactions* 9(7):574-583.
29. Lavenus J, et al. (2013) Lateral root development in *Arabidopsis*: fifty shades of auxin. *Trends in Plant Science* 18(8):455-463.

30. Ni J, Shen Y-X, Zhang Y-Y, & Liu Y (2014) Histological characterization of the lateral root primordium development in rice. *Botanical Studies* 55.
31. Kitomi Y, Inahashi H, Takehisa H, Sato Y, & Inukai Y (2012) OsIAA13-mediated auxin signaling is involved in lateral root initiation in rice. *Plant Science* 190:116-122.
32. Inukai Y, et al. (2005) Crown rootless1, which is essential for crown root formation in rice, is a target of an AUXIN RESPONSE FACTOR in auxin signaling. *Plant Cell* 17(5):1387-1396.
33. Liu H J, et al. (2005) ARL1, a LOB-domain protein required for adventitious root formation in rice. *Plant Journal* 43(1):47-56.

Example 2: CO4 does not Promote Root System Development in Legumes

This example shows that the results obtained in Example 1 using rice, a non-leguminous mycorrhizal plant model, cannot be replicated in legumes. Specifically, we demonstrate that in *M. truncatula*, stimulation of lateral root emergence occurred following treatment with Myc-LCOs, but not following treatment with CO4. In contrast, Example 1 showed that both Myc-LCOs and CO4 (along with CO8) promoted increased root system development in rice. This work indicates that legumes and non-legumes differ in their perception of Myc-LCO and CO signals, suggesting that legume and nonlegume species respond to different components in the mix of signals produced by arbuscular mycorrhizal fungi.

Results

LCOs, CO4, and CO8 Promote Root Development in Rice, while LCOs, but not COs, Promote Root Development in the Legume *M. truncatula*.

Figure 7:
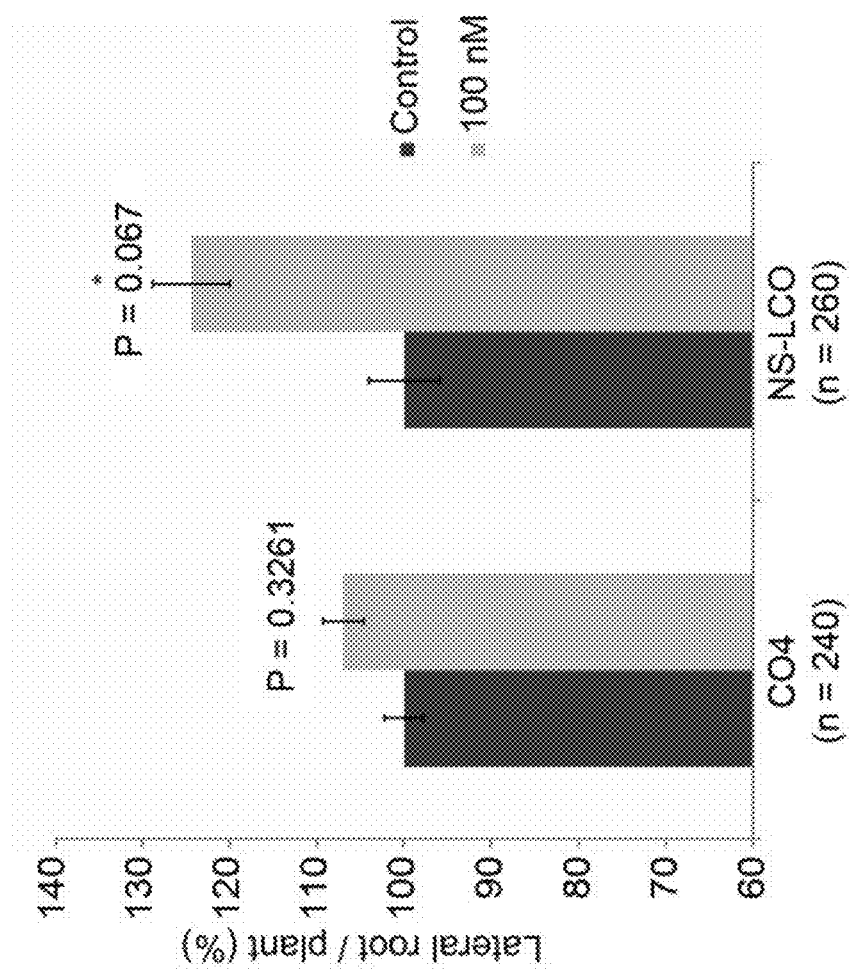
FIG. 7 shows promotion of lateral root emergence in *M. truncatula* by NS-LCO, but not by CO4. *M. truncatula* roots were treated with $10^{-7}$ M CO4 or $10^{-7}$ M NS-LCO and the effect on lateral root emergence was measured. The numbers in parentheses indicate the number of plants analyzed. The significance of the difference to the treated control plants, as measured using a t-test, is indicated. The treatments are measured as fold induction relative to the control. Error bars represent the standard error.

We tested the promotion of lateral root outgrowth in rice by S-LCO, NS-LCO, CO4, and CO8, and found that all four molecules could promote lateral root outgrowth and enhance overall root system growth (see Example 1). In contrast to what we observed in rice, using the protocol of Example 1, CO4 could not induce lateral root emergence in *M. truncatula* (FIG. 7), but the Myc-LCOs can activate this response (Maillet, F., et al. (2011), Nature 469: 58-63). This demonstrates that legumes and non-legumes differ fundamentally in their response to the spectrum of Myc-LCOs and COs for modifications to root architecture. Accordingly, the disclosed method is limited in scope to treating non-leguminous plants, or seeds, seedlings or plant parts thereof.

Example 3: The Effect of CO4 and CO8 Seed Treatment on Growth and Development of Hard Red Spring Wheat, Rice and Corn This example demonstrates that CO4 and/or CO8 when applied to the seeds of three different grain crop plants, promotes the growth of the plants, as measured by one or more parameters of plant growth or development.

Experiment 1: Effects of CO4 and CO8 Treatment on Hard Red Spring Wheat (HRSW) In Vitro Methods Hard red spring wheat seeds were surface sterilized using ethanol and bleach. The sterilized seeds were then divided among 4 treatment groups of 5 grams each into 50 ml falcon tubes. To the control tube, 0.5% ethanol in water was added. To the CO4 tube, 125 µl of $10^{-6}$ M CO4 solution was added. To the CO8 tube, 125 µl of $10^{-6}$ M CO8 solution was added. To the "Consensus" tube, 125 µl of $10^{-6}$ M solution of chitosan (CONSENSUS® chitosan; Loveland Products, Inc., Loveland, Colo.) was added. Each tube was then shaken to coat the seeds. The coated seeds were then placed on sterile Petri dishes in a hood and were left to dry overnight in the hood.

The seeds were then germinated on damp germination paper in sterile Petri dishes for 4 days. The resulting seedlings were transferred to Fahräeus medium plates containing damp germination paper, and the plates were wrapped in Parafilm®. Fahräeus medium contains 0.5 m M $MgSO_4$, 0.7 mM $KH_2PO_4$, 0.4 mM $Na_2HPO_4$, 0.02 mM Fe-EDTA, 0.01 mM $MnSO_4$, 0.007 mM $CuSO_4$, 0.006 mM $ZnSO_4$, 0.016 mM $H_3BO_3$, 0.001 mM $Na_2MoO_4$, and 15 g/L Agar for plant tissue, adjusted to pH 6.5 before autoclaving. The plants were grown at room temperature under continuous light for 4-5 days. The number of primary roots (PR), lateral roots (LR), root system length (RSL) and dry weight (DW) was then measured for all plants.

Results

The results are tabulated in Table 1 below:

TABLE 1

Measured Parameters for Control, CO8, CO4 and Consensus Treatment Groups (Wheat)

| Treatment | Number of Primary Roots | Number of Lateral Roots | Root System Length (cm) | Dry Weight (g) |
| --- | --- | --- | --- | --- |
| Control | 5.64 | 3.21 | 11.82 | 0.0194 |
| CO8 | 5.20 | 3.00 | 11.51 | 0.0191 |
| CO4 | 5.20 | 3.73 | 13.21* | 0.0206 |
| Consensus | 5.27 | 3.53 | 11.52 | 0.0213 |

*Significant difference at $P < 0.05$

Figure 8:
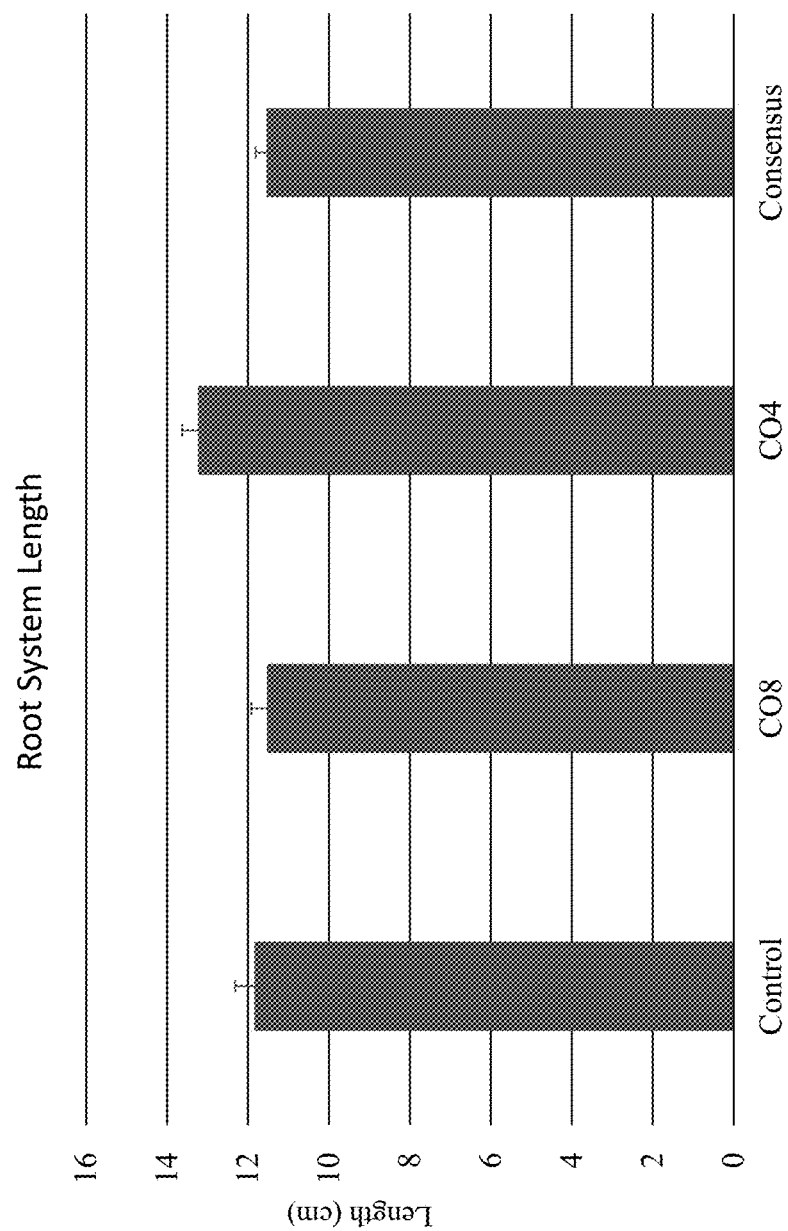
FIG. 8 shows the in vitro effect of seed application on HRSW root system length. Compared with control treatment, CO4 treatment significantly promoted root growth. One star (*) indicates significant difference at the P<0.05 (n=15).

CO4 treatment significantly increased root system length over the control (see also FIG. 8), indicating that the treatment facilitates at least one growth parameter in wheat.

Experiment 2: Effects of CO4 and CO8 Treatment on Hard Red Spring Wheat in Pots Methods Five grams of hard red spring wheat seeds were added to three separate 50 ml tubes. A water solution containing 0.5% ethanol was added to the control tube, 125 µl of $10^{-6}$ M CO4 solution was added to the CO4 tube, and 125 µl of $10^{-6}$ M CO8 solution was added to the CO8 tube. Each tube was then shaken to coat the seeds. Seeds were potted immediately following treatment into moistened SUNGRO® potting mix in 4×6×6 cm pots. Plants were watered by pouring water into the tray containing the pots up to about ¾ inch high.

After sowing the seeds, the pots were randomly distributed (16 pots per treatment) throughout the tray and placed underneath continuous light at room temperature for 1 week. Liquid Fahräeus medium (plant fertilizer solution; see above) was applied every 2 days or when necessary. After a week, the pots were placed underneath 10 h light and 14 h dark cycle at room temperature for 1 week. After 1 week underneath 10 h light and 14 h dark cycle (2 weeks after planting), the plants were carefully removed from the pots, and as much soil as possible was shaken off. The remaining soil was removed by submerging the root system into a beaker of water.

The number of primary roots (PR), lateral roots (LR), root system length (RSL) and dry weight (DW) was then measured for all plants.

Results

The results are tabulated in Table 2 below:

TABLE 2

Measured Parameters for Control, CO8 and CO4 Treatment Groups (Wheat)

| Treatment | Number of Primary Roots | Number of Lateral Roots | Root System Length (cm) | Dry Weight (mg) |
|---|---|---|---|---|
| Control | 3.30 | 14.45 | 10.70 | 24.03 |
| CO8 | 3.35 | 14.30 | 12.22 | 32.38* |
| CO4 | 3.15 | 16.25 | 11.75 | 30.20* |

*Significant difference at $P < 0.05$

Figure 9:
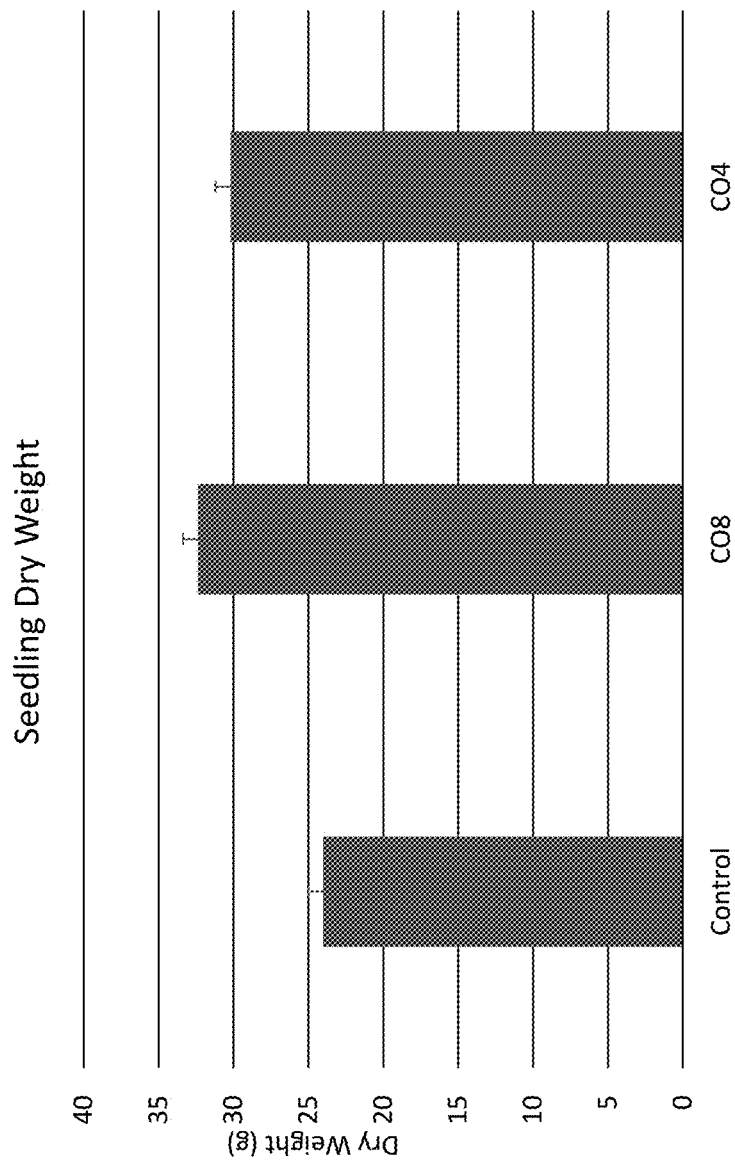
FIG. 9 shows the "in pot" effect of seed application on HRSW seedling growth. Compared with control treatment, CO4 and CO8 treatment significantly promoted plant growth. One star (*) indicates significant difference at the P<0.05 (n=20).

Both CO4 and CO8 seed treatments significantly increased dry weight (a measurement of total plant growth) in the wheat plants (see also FIG. 9), confirming that such treatments facilitate plant growth in wheat. A similar dry weight increase was not shown with plants grown in plates in Experiment 1 above, likely because of the limitations on growth that plates impose. Average root system length was also higher for both CO4 and CO8 treatments, although the increased length was not great enough to be significant at $P<0.05$.

Together, the results of Experiment 1 and 2 demonstrate that CO4 and/or CO8 treatment of wheat seeds facilitates growth and development of the wheat plants that germinate from the treated seeds.

Experiment 3: Effects of CO4 and CO8 Treatment on Rice In Vitro

Methods

Rice seeds were sterilized using 2% bleach. The sterilized seeds were then divided among 3 treatment groups of 10 seeds each into 15 ml falcon tubes. To the control tube, 0.5% ethanol in water was added. To the CO4 tube, 100 µl of $10^{-6}$ M CO4 solution was added. To the CO8 tube, 100 µl of $10^{-6}$ M CO8 solution was added. Each tube was then shaken to coat the seeds. The coated seeds were then placed on sterile Petri dishes in a hood and were left to dry overnight in the hood.

The seeds were then germinated on damp germination paper in sterile Petri dishes for 5 days. The resulting seedlings were transferred to Fahräeus medium plates containing damp germination paper, and the plates were wrapped in Parafilm®. The roots part of the plate was covered with aluminum foil. The plants were grown at room temperature under continuous light for 33 days. The length of the shoot and root systems was measured for all plants.

Results

Figure 10:
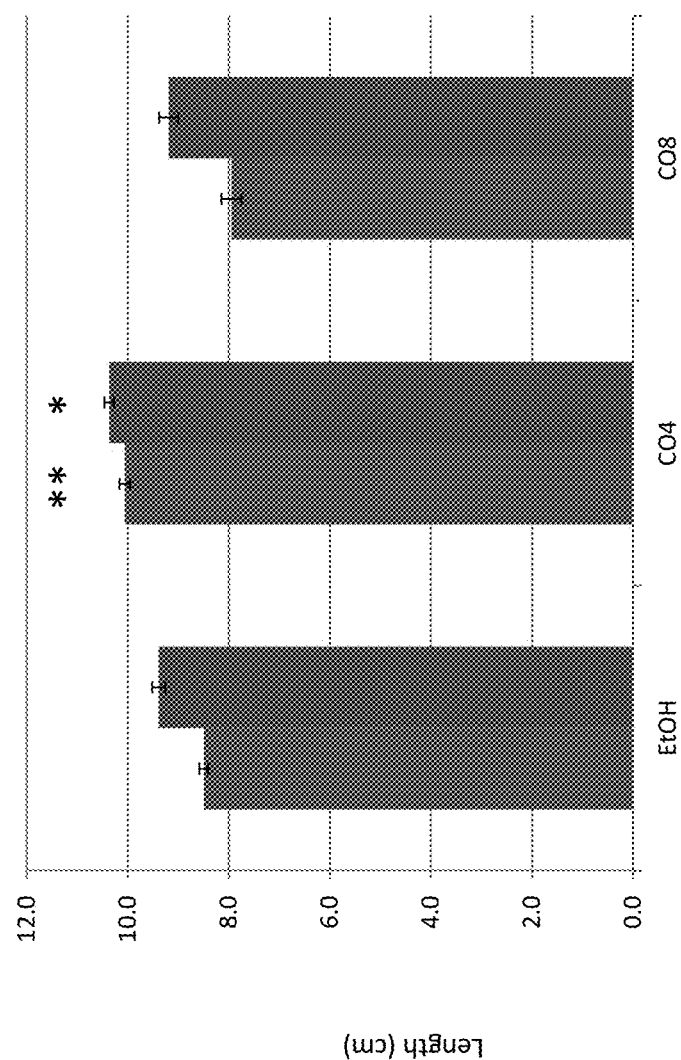
FIG. 10 shows the effect of seed application on rice shoot and root length. Rice seeds were treated with three different solutions of 0.5% ethanol (control), $10^{-6}$ M CO4, or $10^{-6}$ M CO8, and grown on modified Fahraeus medium for 33 days. The length of roots (left bar) and shoots (right bar) were measured. Compared with ethanol treatment, CO4 treatment significantly promoted shoot and root growth. One star (*)

CO4 treatment significantly increased both shoot and root system length compared with the ethanol control (see FIG. 10). This data supplements the data disclosed in Example 1 above indicating that both CO4 and CO8 treatment can be used to facilitate growth and development in rice.

Experiment 4: Effects of CO4 and CO8 Treatment on Corn in Pots

Methods

Five grams of corn (maize) seeds were added to three separate 50 ml tubes. A water solution containing 0.5% ethanol was added to the control tube, 125 µl of $10^{-6}$ M CO4 solution was added to the CO4 tube, and 125 µl of $10^{-6}$ M CO8 solution was added to the CO8 tube. Each tube was then shaken to coat the seeds. Seeds were potted immediately following treatment into moistened SUNGRO® potting mix in 4×6×6 cm pots. Plants were watered by pouring water into the tray containing the pots up to about ¾ inch high.

After sowing the seeds, the pots were randomly distributed (16 pots per treatment) throughout the tray and placed underneath continuous light at room temperature for 1 week. Liquid Fahräeus medium (plant fertilizer solution; see above) was applied every 2 days or when necessary. After a week, the pots were placed underneath 10 h light and 14 h dark cycle at room temperature for 1 week. After 1 week underneath 10 h light and 14 h dark cycle (2 weeks after planting), the plants were carefully removed from the pots, and as much soil as possible was shaken off. The remaining soil was removed by submerging the root system into a beaker of water.

The number of primary roots (PR), lateral roots (LR), root system length (RSL) and dry weight (DW) was then measured for all plants.

Results

The results are tabulated in Table 3 below. As shown in Table 3 and FIG. 11, corn plants resulting from seeds receiving both CO4 and CO8 treatments exhibited increased number of lateral roots, as compared to corn plants resulting from seeds receiving the control treatment. However, the increased lateral root development with CO8 treatment was not great enough to be significant at $P<0.1$, likely due to high variability. CO4 did significantly increase lateral root growth at $P<0.1$. This experiment demonstrates that the disclosed seed treatment method can be used to facilitate growth in corn.

TABLE 3

Measured Parameters for Control, CO8 and CO4 and Treatment Groups (Corn)

| | Average | | | |
|---|---|---|---|---|
| Treatment | Seminal Roots | Lateral Roots | Root System Length | Dry Weight |
| Control | 4.40 | 38.95 | 21.53 | 0.1176 |
| CO4 | 4.45 | 45.00* | 23.76 | 0.1225 |
| CO8 | 4.75 | 44.95 | 21.42 | 0.1229 |

*Significant difference at $P < 0.1$

Example 4: The Effect of CO4 and CO8 Foliar Treatment on Root/Shoot Growth of Rice This example extends the results of the previous examples to foliar treatment in rice. Specifically, foliar treatment with CO4 in rice is shown to facilitate both shoot growth and root growth.

Methods

Rice seeds were surface sterilized using 2% bleach. Seeds were then germinated on damp germination paper in sterile Petri dishes for 5 days. The seedlings were then transferred to Fahraeus medium plates containing damp germination paper. The plates were wrapped in Parafilm®, and the roots part of the plate covered with aluminum foil.

The plants were grown at room temperature under continuous light for 21 days. The plants were then transferred to moistened SUNGRO® soil pots (8×8×10 cm) and grown for 3 days under greenhouse condition. The plants were hydrated by pouring water into the tray underneath the pots.

The soil surface was then covered with plastic wrap to prevent any liquid droplets from contacting the soil. Using painting brushes, the front, and back of the plant leaves were treated with 3 ml of chitin derived compounds (CO4 and CO8) at $10^{-6}$ M or a control (0.5% ethanol), each including 0.05% of Silwet L-77 (surfactant). Eleven plants were treated with each solution. The plants were subsequently grown for 14 days, and the shoot length was measured. Once a week, half-strength Hoagland solution was added into the trays underneath the pots. The plants were grown for another 4 days, and the lengths of the shoot and root systems were measured.

Results

Figure 12A:
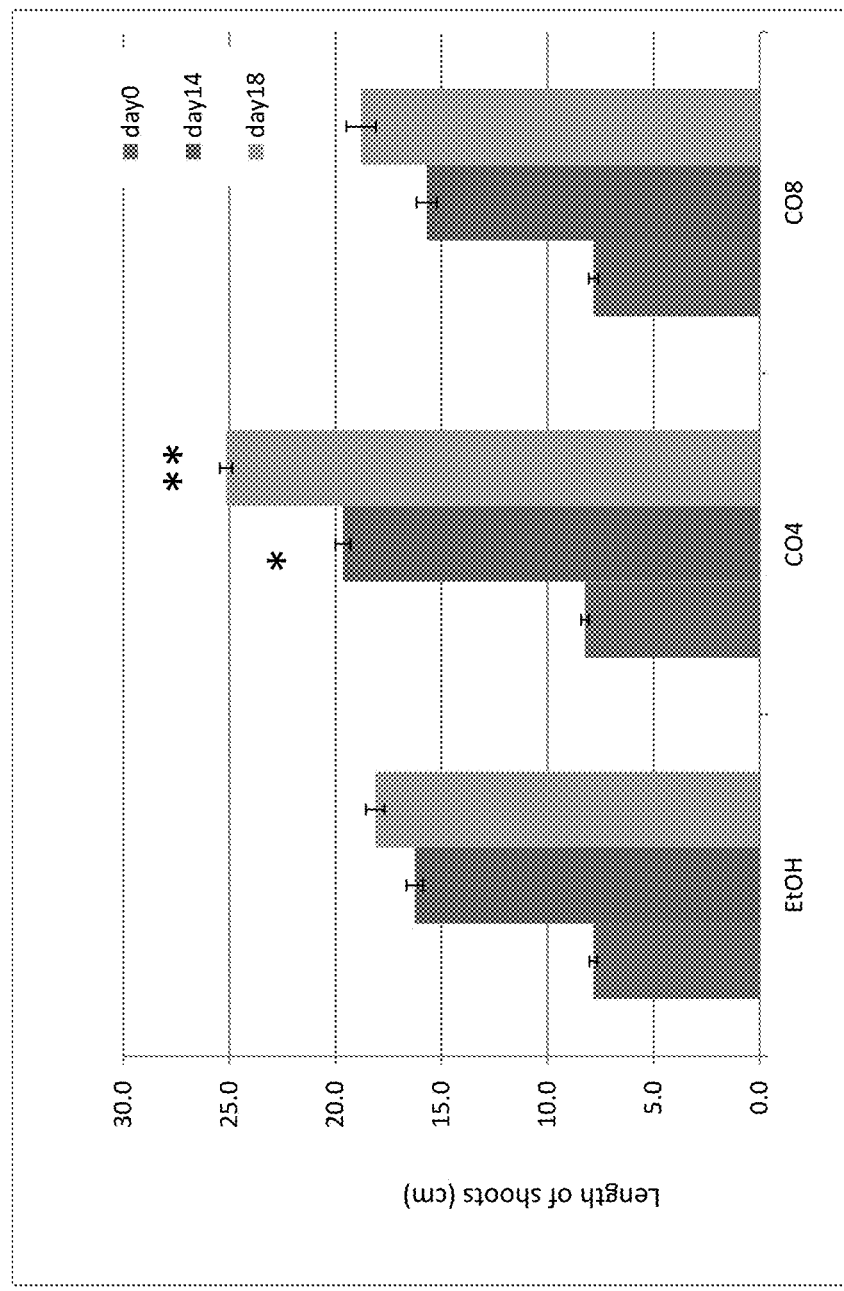
Figure 12B:
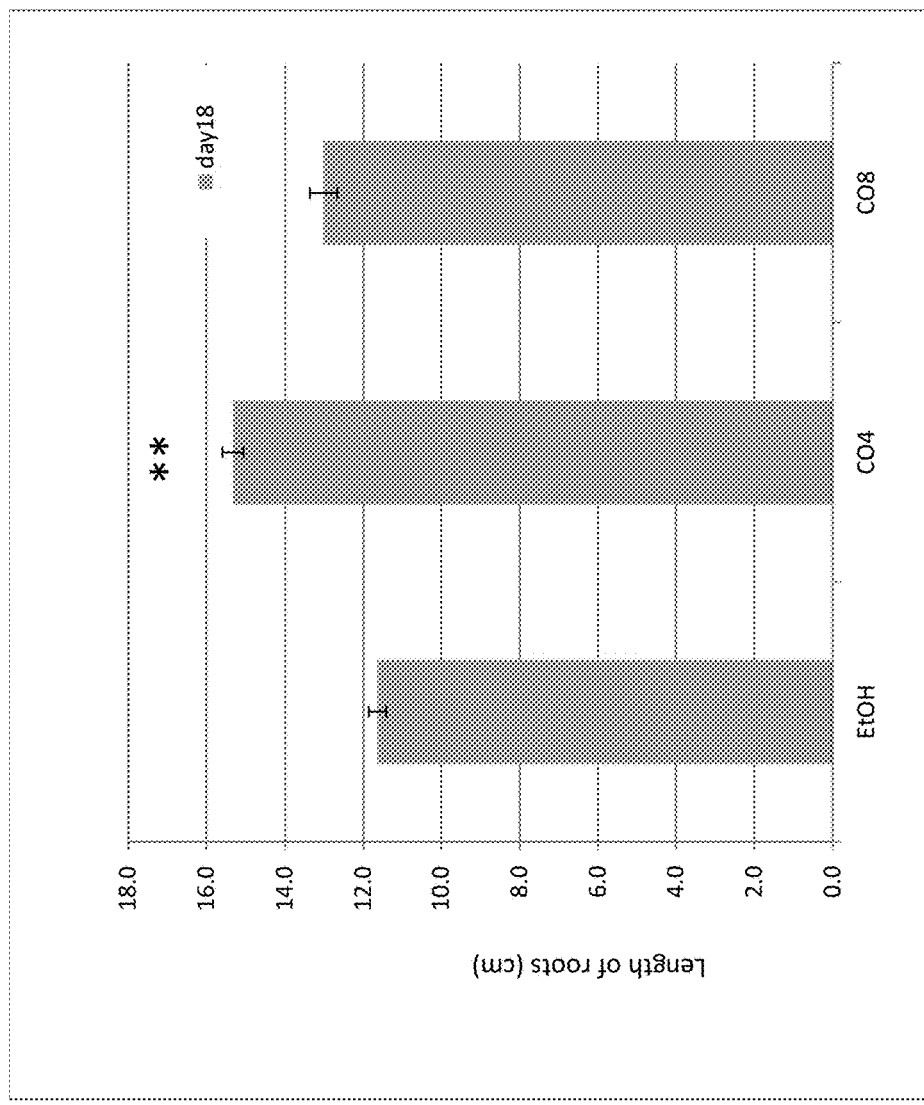

CO4 foliar treatment on rice significantly increased shoot length at day 14 after treatment, and the significance was even higher at day 18 (FIG. 12A). CO4 treatment also significantly promoted root system length at day 18 (FIG. 12B). In sum, this example shows that foliar application of CO4 in rice promotes plant growth in the rice.

Example 5: CO4 and CO8 Seed Treatment Reduce Root Growth in an Exemplary Legume

Consistent with the results reported in Example 2, this example confirms that the results reported in various non-leguminous plants (see Examples 1, 3 and 4) cannot be replicated in legumes. Thus, the disclosed method is limited to non-leguminous plants.

Methods

Five grams of pea seeds (the legume *Pisum sativum*) were added to three separate 50 ml tubes. A water solution containing 0.5% ethanol was added to the control tube, 125 µl of $10^{-6}$ M CO4 solution was added to the CO4 tube, and 125 µl of $10^{-6}$ M CO8 solution was added to the CO8 tube. Each tube was then shaken to coat the seeds. Seeds were potted immediately following treatment into moistened SUNGRO® potting mix in 4×6×6 cm pots. Plants were watered by pouring water into the tray containing the pots up to about ¾ inch high.

After sowing the seeds, the pots were randomly distributed (16 pots per treatment) throughout the tray and placed underneath continuous light at room temperature for 1 week. Liquid Fahräeus medium (plant fertilizer solution; see above) was applied every 2 days or when necessary. After a week, the pots were placed underneath 10 h light and 14 h dark cycle at room temperature for 1 week. After 1 week underneath 10 h light and 14 h dark cycle (2 weeks after planting), the plants were carefully removed from the pots, and as much soil as possible was shaken off. The remaining soil was removed by submerging the root system into a beaker of water.

The number of primary roots (PR), lateral roots (LR), root system length (RSL) and dry weight (DW) were then measured for all plants.

Results

The results are tabulated in Table 4 below:

TABLE 4

Measured Parameters for Control, CO8 and CO4 Treatment Groups (Peas) Average

| Treatment | Primary Roots | Lateral Roots | Tap Root Length | Dry Weight |
|---|---|---|---|---|
| Control | 18.45 | 22.45 | 10.31 | .15 |
| CO4 | 14.20* | 13.35* | 10.25 | .13 |
| CO4 | 15.50* | 15.00* | 10.28 | .14 |

*Significant difference at P < 0.05

In contrast to the results demonstrated with non-leguminous plants, CO4, and CO8 seed treatments significantly decreased the number of primary and lateral roots of pea seedlings compared to the control. None of the other variables were affected by the CO treatment.

Together, the results of Example 2 and this example demonstrate that the disclosed chitin oligomers cannot be used to promote the growth and/or development of leguminous plants. Accordingly, the disclosed method is limited to promoting the growth and/or development of non-leguminous plants.

The examples and embodiments described herein are for illustrative purposes only. Various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for stimulating the growth of a non-leguminous plant, comprising contacting a non-leguminous plant, a part thereof, or a seedling or seed thereof with a composition comprising a chitooligosaccharide (CO) having the formula:

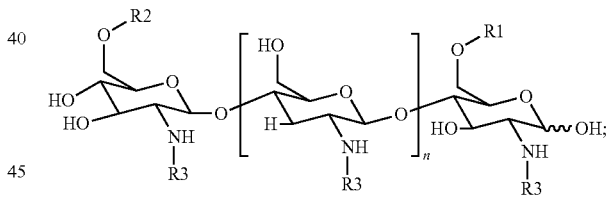

wherein n is 2;
R1 is —H;
R2 is —H; and
each R3 is —COCH$_3$ (the compound is tetra-N-acetyl-chitotetraose, CO4);
whereby the growth of the plant is stimulated.

2. The method of claim 1, wherein the composition is contacted with one or more leaf or root surfaces of the non-leguminous plant.

3. The method of claim 2, wherein the composition further comprises a surfactant.

4. The method of claim 1, wherein the composition is contacted with a seedling, seedling part or seed of the non-leguminous plant.

5. The method of claim 4, wherein the seedling part or seed of the non-leguminous plant is submerged in and subsequently removed from the composition.

6. The method of claim 1, wherein the composition is contacted with the plant, plant part, seedling or seed for about 1 hour to about 96 hours.

7. The method of claim 6, wherein the composition is contacted with the plant, plant part, seedling or seed for about 6 hours to about 48 hours.

8. The method of claim 1, wherein the concentration of the CO in the composition is within the range of about $10^{-3}$ M to about $10^{-10}$ M.

9. The method of claim 8, wherein the concentration of the CO in the composition is within the range of about $10^{-3}$ M to about $10^{-9}$ M.

10. The method of claim 9, wherein the concentration of the CO in the composition is within the range of about $10^{-3}$ M to about $10^{-8}$ M.

11. The method of claim 1, wherein the composition further comprises water and alcohol.

12. The method of claim 11, wherein the alcohol is ethanol.

13. The method of claim 1, wherein the non-leguminous plant is a monocotyledon.

14. The method of claim 13, wherein the monocotyledon is a cereal grain.

15. The method of claim 14, wherein the cereal grain is selected from the group consisting of rice, wheat, and corn.

16. The method of claim 1, wherein the growth of the non-leguminous plant that is stimulated is selected from the group consisting of increased number of crown roots, increased number of lateral roots, increased root length, increased dry weight, increased shoot length, and combinations thereof, as compared to the same quantity measured in the same type of non-leguminous plant wherein the plant, part thereof, or seedling or seed thereof has not been contacted with the composition.

* * * * *

UNITED STATES PATENT AND TRADEMARK OFFICE
CERTIFICATE OF CORRECTION

PATENT NO. : 10,149,472 B2
APPLICATION NO. : 15/185587
DATED : December 11, 2018
INVENTOR(S) : Jean-Michel Ané, Audrey Kalil and Junko Maeda It is certified that error appears in the above-identified patent and that said Letters Patent is hereby corrected as shown below:

Column 18, Claim 1, the chemical formula shown in Lines 38-46 should appear as follows:

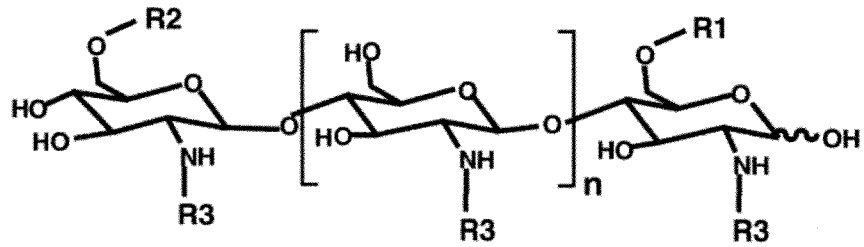

Signed and Sealed this
Twenty-ninth Day of January, 2019

Andrei Iancu
*Director of the United States Patent and Trademark Office*